(12) United States Patent
Poulsen et al.

(10) Patent No.: US 8,379,794 B2
(45) Date of Patent: Feb. 19, 2013

(54) METHOD TO ESTIMATE POSITION, MOTION AND TRAJECTORY OF A TARGET WITH A SINGLE X-RAY IMAGER

(75) Inventors: Per Rugaard Poulsen, Aabyhoej (DK); Byungchul Cho, Palo Alto, CA (US); Katja Langen, Orlando, FL (US); Patrick Kupelian, Winter Park, FL (US); Paul J. Keall, Palo Alto, FL (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 108 days.

(21) Appl. No.: 12/584,227

(22) Filed: Sep. 1, 2009

(65) Prior Publication Data

US 2010/0172469 A1 Jul. 8, 2010

Related U.S. Application Data

(60) Provisional application No. 61/191,348, filed on Sep. 5, 2008.

(51) Int. Cl.
*A61N 5/10* (2006.01)
(52) U.S. Cl. ................ 378/65; 378/20; 378/62
(58) Field of Classification Search .......... 378/20, 378/62, 65
See application file for complete search history.

(56) References Cited

U.S. PATENT DOCUMENTS

| | | | | |
|---|---|---|---|---|
| 5,289,562 | A * | 2/1994 | Mizuta et al. | 704/200 |
| 6,718,309 | B1 * | 4/2004 | Selly | 704/503 |
| 7,227,925 | B1 * | 6/2007 | Mansfield et al. | 378/65 |
| 2004/0015073 | A1 * | 1/2004 | Schell et al. | 600/411 |
| 2005/0074084 | A1 * | 4/2005 | Wang et al. | 378/4 |
| 2006/0050847 | A1 * | 3/2006 | Jaffray et al. | 378/65 |
| 2008/0162183 | A1 * | 7/2008 | Sachanandani et al. | 705/2 |

FOREIGN PATENT DOCUMENTS

WO WO2009091382 7/2009

* cited by examiner

*Primary Examiner* — Hoon Song
*Assistant Examiner* — Mona M Sanei
(74) *Attorney, Agent, or Firm* — Lumen Patent Firm

(57) ABSTRACT

The present invention provides a method for estimation of retrospective and real-time 3D target position by a single imager. The invention includes imaging a target on at least one 2D plane to determine 2D position and/or position components of the target, and resolving a position and/or position component along at least one imager axis of the target using a spatial probability density. The present invention provides a probability-based method for accurate estimation of the mean position, motion magnitude, motion correlation, and trajectory of a tumor from CBCT projections. The applicability of the method for tumors with periodic respiratory motion and for prostate are provided. Clinical feasibility is demonstrated for a pancreas tumor. The method includes monoscopic tracking of the 3D prostate position utilizing the spatial probability density to estimate the unresolved motion from the resolved motion. The method is applicable to prostate tracking even with a population-based probability density.

16 Claims, 15 Drawing Sheets

US 8,379,794 B2

METHOD TO ESTIMATE POSITION, MOTION AND TRAJECTORY OF A TARGET WITH A SINGLE X-RAY IMAGER

CROSS-REFERENCE TO RELATED APPLICATIONS

This application is cross-referenced to and claims the benefit from U.S. Provisional Application 61/191,348 filed Sep. 5, 2008, and which are hereby incorporated by reference.

STATEMENT REGARDING FEDERALLY SPONSORED RESEARCH OR DEVELOPMENT

The present invention was supported in part by grant number R01CA093626 from the US National Cancer Institute. The U.S. Government has certain rights in the invention.

FIELD OF THE INVENTION

The invention relates generally to radiotherapy. More particularly, the invention relates to a method for 3-D target position estimation with a single x-ray imager.

BACKGROUND

In recent years, cone-beam CT (CBCT) has been integrated with linear accelerators for volumetric imaging of the patient anatomy at radiotherapy treatments. Proposed or implemented usage of CBCT in radiotherapy includes patient setup based on bony structures and soft tissue, recalculation of patient dose, and adaptive radiotherapy. Under the assumption of periodic motion, CBCT projections can be sorted into sub-period phases that can be reconstructed separately to form static volumetric images for each respiratory phase. Although such four-dimensional CBCT scans provide the mean patient anatomy in each phase, variations in the respiratory cycles and non-periodic motion such as prostate motion are not resolved. The main focus in these CBCT applications has been on the reconstructed volumetric images, whereas the CBCT projections themselves are merely regarded as an intermediate step toward the reconstruction. In many institutions, the CBCT projections are deleted after creation of the volumetric images. However, when radiopaque markers are used as tumor surrogates, their positions on each CBCT projection contain valuable information about the tumor motion during the CBCT acquisition. The projections provide two-dimensional (2D) information of the tumor trajectory in a rotating coordinate system. Reconstruction of the actual three-dimensional (3D) tumor trajectory from the projections cannot be made without ambiguity because an infinite number of 3D trajectories result in the same sequence of projections.

The development of volumetric-modulated arc therapy has enabled efficient delivery of complex radiotherapy dose distributions within a single gantry rotation. The high conformity of the dose distribution to the target volume increases the accuracy requirements in the treatment delivery. In the case of prostate cancer this is especially true for hypofractionated radiotherapy, where recent studies have suggested that safe delivery may require real-time prostate position monitoring during treatment and correction strategies to compensate for occasional large intrafraction prostate motion.

The current state of the art has, in a clinical setting, combined real-time prostate position monitoring with motion compensation by periodic realignment of the treatment beam. The required target position signal during treatment delivery is provided by stereoscopic x-ray imaging, i.e. pairs of simultaneous x-ray images of implanted markers acquired every 30-60 sec.

Although still lacking integration with real-time motion compensation, intrafraction prostate position monitoring with stereoscopic x-ray imaging has also been implemented clinically for conventional gantry-mounted linear accelerators. The imaging has been performed with kV imager pairs that either rotate with the gantry or are mounted in stationary positions in the treatment room. Alternatively, intrafraction prostate position monitoring can be performed with implanted electromagnetic transponders.

While kV imager pairs are not standard equipment, many modern linear accelerators are equipped with a single gantry-mounted kV x-ray imager that enables x-ray imaging perpendicular to the MV treatment beam. Target position monitoring can be performed with stereoscopic imaging based on the kV imager and MV portal imaging. Use of portal images is attractive because it does not pose additional dose to the patient, but a high degree of beam modulation by the MLC leaves will often hinder target (surrogate) visibility on the portal images. Also, the implanted markers may be too small to be visible in MV images.

Accordingly, there is a need to develop a method to estimate the three-dimensional (3D) target position from the two-dimensional (2D) projections on a single imager and the 3D probability density function (PDF) for the target and apply the method for estimation of the 3D target trajectory from the projected 2D trajectory in a series x-ray images in very accurate trajectory estimations with estimation errors less than 1 mm for both prostate and tumors with respiratory motion. Further, there is a need to extend retrospective trajectory estimation to prospective real-time trajectory estimation in order to allow actions to be taken to account for the target motion (e.g. tracking or treatment interruptions).

SUMMARY OF THE INVENTION

The present invention provides a method for estimation of retrospective and real-time 3D target position by a single imager. The invention includes imaging a target on at least one 2D plane to determine 2D position components of the target, and resolving a position component along at least one imager axis of the target using a spatial probability density.

According to one aspect of the invention, the spatial probability density for the target position comprises a Gaussian probability distribution.

In a further aspect, the spatial probability density is centered at an isocenter of a treatment unit, at a center of a patient coordinate system, or any other point in space.

In another aspect of the invention, the spatial probability density is determined from a variance and covariance matrix of the target position.

According to another aspect of the invention, determining the 2D position includes projecting the target into a point on at least a 2-D imager plane disposed on at least one imaging angle relative to a vertical direction, where the target lies along a ray line between the point on the imager plane and a beam source of an imager.

In yet another aspect of the invention, resolving the position component along an imager axis includes using a maximum likelihood estimation to determine a best fit of projection data to a spatial Gaussian distribution of a probability density of the target position, and determining an expectation value or the target position along the ray line. Here, an uncertainty in target position estimation along the ray line is determined from a one-dimensional probability density for the target along the ray line. Further, more than one imager can be used without being synchronized. Additionally, the Gaussian distribution includes a mean target position, a standard deviation of the mean target position, and correlation coefficients of paired degrees of freedom of the target position. Here, the mean target position, the standard deviation, and the correlation coefficients can be used for motion inclusive radiotherapy. In another aspect, the expectation value along the ray line is used to estimate an unresolved target position component as a function of the resolved the target position component(s). Further, the expectation value is used to determine a trajectory of the target, where the determined target trajectory is a real-time determination and the determined target trajectory is used for gating and target tracking during radiotherapy. Here, the gating and target tracking is done in real-time using a dynamic multi-leaf collimator, a treatment couch or other device to align the treatment beam and the target.

In another aspect of the invention, the imaging of target on the 2D plane is done in a time ranging from continuous imaging to intervals if several minutes.

In yet another aspect of the invention, the imager can include at least one x-ray imager, where the at least one x-ray imager is operated independently or simultaneously and can be a kilovolt x-ray imager, a megavolt x-ray imager.

In a further aspect, a beam of the imager is disposed perpendicular to a treatment beam.

According to another aspect of the invention, the estimation is done in real-time during a treatment therapy such as intensity modulated arc therapy, arc radiotherapy, intensity-modulated radiotherapy from fixed fields or conformal radiotherapy.

BRIEF DESCRIPTION OF THE FIGURES

The objectives and advantages of the present invention will be understood by reading the following detailed description in conjunction with the drawing, in which.

DETAILED DESCRIPTION OF THE INVENTION

Although the following detailed description contains many specifics for the purposes of illustration, anyone of ordinary skill in the art will readily appreciate that many variations and alterations to the following exemplary details are within the scope of the invention. Accordingly, the following preferred embodiment of the invention is set forth without any loss of generality to, and without imposing limitations upon, the claimed invention.

The present invention provides a method for estimation of retrospective and real-time 3D target position by a single imager. The invention includes imaging a target on at least one 2D plane to determine 2D position and/or position components of the target, and resolving a position and/or position component along at least one imager axis of the target using a spatial probability density.

According to the invention, the method for estimation of mean position, motion magnitude, and trajectory of a tumor from CBCT projections has accuracy typically much better than 1 mm. The method is applicable to motion-inclusive, respiratory-gated, and tumor-tracking radiotherapy. The invention makes it possible to give a good estimate of the 3D trajectory with a probabilistic approach.

The inventors have simulated CBCT acquisition for more than 80 hours of patient-measured trajectories for thoracic/abdominal tumors and prostate. The trajectories were divided into 60-second segments for which CBCT was simulated by projecting the tumor position onto a rotating imager. Tumor (surrogate) visibility on all projections was assumed. The mean and standard deviation of the tumor position and motion correlation along the three axes were determined with maximum likelihood estimation based on the projection data, assuming a Gaussian spatial distribution. The unknown position component along the imager axis was approximated by its expectation value, determined by the Gaussian distribution. Transformation of the resulting three-dimensional position to patient coordinates provided the estimated trajectory. Two trajectories were experimentally investigated by CBCT acquisition of a phantom.

The root-mean-square error of the estimated mean position was 0.05 mm. The root-mean-square error of the trajectories was <1 mm in 99.1% of the thorax/abdomen cases and in 99.7% of the prostate cases. The experimental trajectory estimation agreed with the actual phantom trajectory within 0.44 mm in any direction. Clinical applicability was demonstrated by estimating the tumor trajectory for a pancreas cancer case.

The method is demonstrated for tumors subject to respiratory motion and for prostate activity, both theoretically by CBCT simulations and experimentally by CBCT scanning of a moving phantom. Clinical feasibility of the method is demonstrated for a pancreas cancer case.

Figure 1:
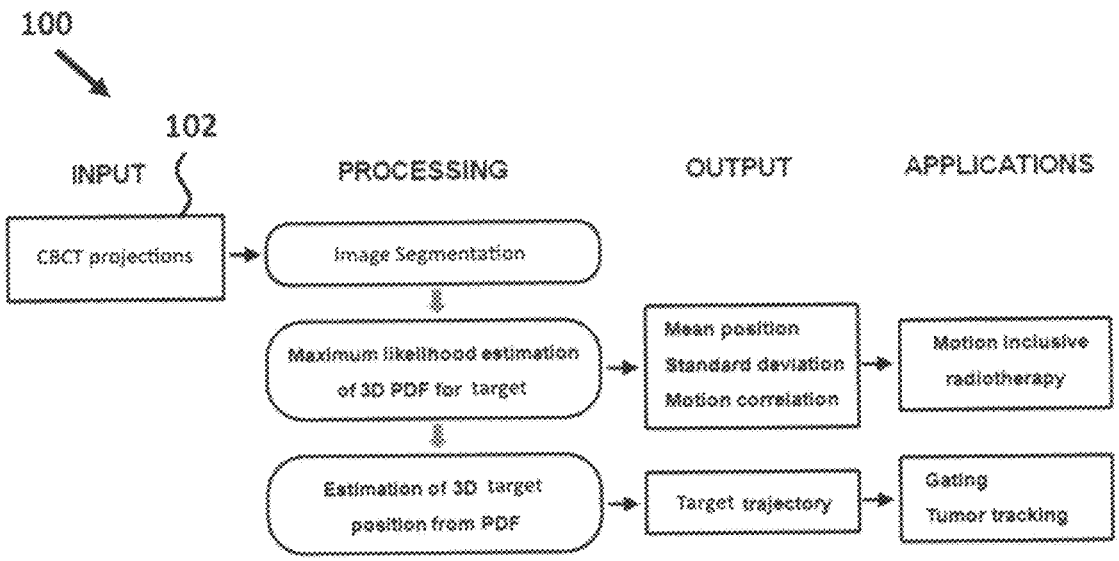
FIG. 1 shows a flow diagram of the estimation method with possible applications, according to the present invention.

The current invention provides a method for estimation of tumor mean position, motion magnitude, and tumor trajectory. The estimation of the tumor trajectory followed two steps:

First, the tumor projections are fitted to a 3D Gaussian distribution. Next, this distribution is used to estimate the tumor trajectory. FIG. 1 provides a schematic overview of the estimation method 100 and some possible applications, where the three-dimensional (3D) Gaussian probability density function (PDF) is first estimated by maximum likelihood estimation and then used for estimation of the unresolved target position perpendicular to the imager, where the Gaussian distribution is an exemplary distribution and other distributions can be used to remain within the spirit of the invention. More specifically, in the first step 102, the 3D Gaussian distribution that best fits the projection data is determined by maximum likelihood estimation (MLE). The Gaussian distribution can be characterized by nine parameters: The mean position ($\mu_{LR}$, $\mu_{CC}$, $\mu_{AP}$) in left-right (LR), cranio-caudal (CC), and anterior-posterior (AP) directions, the standard deviations of the position ($\sigma_{LR}$, $\sigma_{CC}$, $\sigma_{AP}$) in the three directions, and the correlation coefficients of motion along each direction pair: $\rho_{LR-CC}$, $\rho_{LR-AP}$, and $\rho_{CC-AP}$. Knowledge of these nine parameters allows calculation of the probability $P(u,v,\alpha)$ for the tumor to be projected into a point $(u,v)$ on an imager positioned at angle $\alpha$. The total probability of obtaining the observed combination of projections is given by the product $\Pi P(u,v,\alpha)$ of the probabilities for all projections. In the current invention, the parameters of the Gaussian distribution are determined by the MLE method, that is, the parameters are selected such that the total probability $\Pi P(u,v,\alpha)$ is maximized (see FIG. 2a).

The optimization starting point for ($\mu_{LR}$, $\mu_{CC}$, $\mu_{AP}$) is the mean tumor position as estimated by a least square method that minimized the sum of the squared distances between the actual tumor projections and the projections that would result from a static tumor. For each CBCT scan, three optimizations with three sets of starting points for ($\sigma_{LR}$, $\sigma_{CC}$, $\sigma_{AP}$) and ($\rho_{LR-CC}$, $\rho_{LR-AP}$, $\rho_{CC-AP}$) are performed and the one resulting in the highest likelihood is selected. It is understood in the current disclosure that a target need not only be a tumor but could also be a structure that it is desirable for the radiation beam to avoid.

Figure 2:
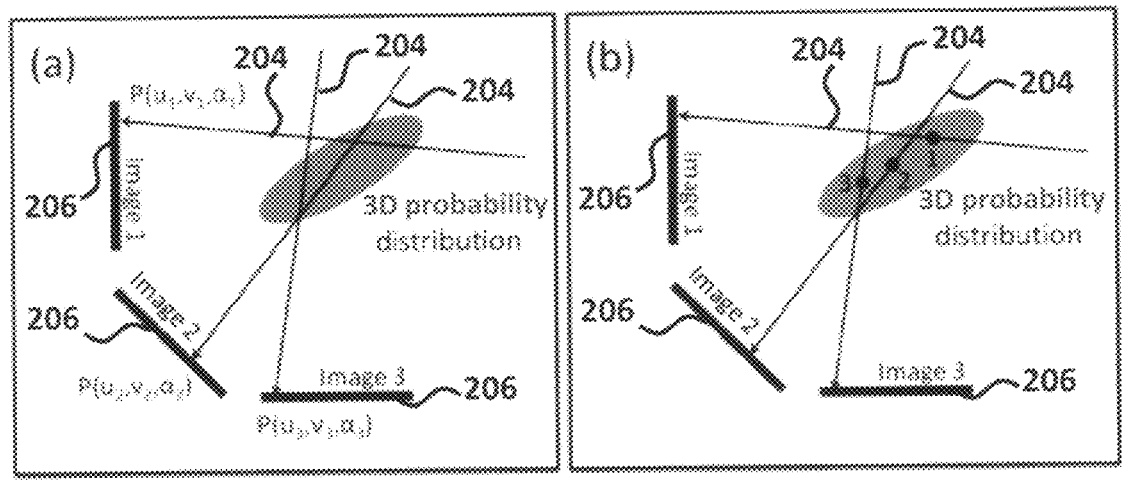
FIGS. 2a-2b show probability-based estimation of tumor trajectory from cone-beam CT projections, according to the present invention.

FIGS. 2a-2b show the probability-based estimation of tumor trajectory from cone-beam CT projections 200. The tumor is projected into imager points $(u_1,v_1)$, $(u_2,v_2)$, $(u_3,v_3)$... for imaging angles $\alpha_1, \alpha_2, \alpha_3$... FIG. 2a shows the first step of the Gaussian probability distribution that maximizes the total probability $P(u_1, v_1, \alpha_1) \times P(u_2, v_2, \alpha_2) \times P(u_3, v_3, \alpha_3) \times \ldots$ being determined by maximum likelihood estimation (indicated by the gray ellipse 202). Again, the Gaussian distribution is an exemplary distribution and other distributions can be used to remain within the spirit of the invention. The lines 204 represent the ray lines from the focus point of the imager system to the projected tumor position on the imager 206. The tumor is known to be located somewhere on these lines 204. For prostate, the LR motion was assumed not to correlate with AP and CC motion, that is, $\rho_{LR-CC}$ and $\rho_{LR-AP}$ are approximated by zero instead of being optimized by the MLE. This was done because it generally gave better results for prostate, most likely because LR prostate motion usually is small and not well correlated with AP and CC motion. For thoracic and abdominal tumors, the generally larger motion ranges and more prominent correlation between LR motion and motion in other directions allowed for inclusion of $\rho_{LR-CC}$ and $\rho_{LR-AP}$ in the MLE optimization.

FIG. 2b shows the second step, where the tumor position along the lines 204 (and thus the three-dimensional [3D] position) is estimated for each projection as the mean position according to the 3D Gaussian, that is, the midpoint of the line's cross section with the gray ellipse (indicated by 1, 2, 3). Here, the unresolved tumor position was estimated for each projection image by using the 3D Gaussian distribution estimated by MLE in the first step. The tumor is known to be located on the line between the focus point of the imaging system and the projection point $(u,v)$ on the imager. The unknown position along this line is estimated as the expectation value determined by the Gaussian distribution (FIG. 2b). Transformation of the resulting 3D positions from imager coordinates to patient coordinates provided the estimated tumor trajectory.

The accuracy of the method according to the invention is established by simulating CBCT acquisition for two large sets of clinical 3D tumor trajectory data. Each trajectory is divided into segments of 60 sec for which CBCT acquisition is simulated.

The simulation for thoracic/abdominal tumors is based on 160 tumor trajectories (46 patients) estimated by a Cyberknife Synchrony system (Accuray, Sunnyvale, Calif.) at Georgetown University Hospital by using a correlation model between internal tumor motion and motion of external surrogates monitored at 25 Hz. The duration of the trajectories ranged from 8 to 110 min, and the total number of 1-min segments for CBCT simulation was 5,113. The mean and maximum motion range for the segments are 2.5 mm and 26.5 mm (LR), 6.8 mm and 56.6 mm (CC), and 3.3 mm and 37.4 mm (AP).

The simulation for prostate is made for 548 trajectories recorded at 10 Hz with implanted electromagnetic transponders (Calypso Medical Technologies, Seattle, Wash.) for 17 patients treated in supine position at M.D. Anderson Cancer Center Orlando. The duration of the trajectories ranged from 3 to 18 min. The total number of 1-min prostate trajectory segments for simulation is 5,323. The mean and maximum motion range for these segments are 0.7 mm and 4.5 mm (LR), 1.5 mm and 17.8 mm (CC), and 1.8 mm and 19.1 mm (AP).

The CBCT simulations are performed by projecting the tumor positions of each trajectory segment onto a flat panel detector that is assumed to rotate 360° clockwise in 60 sec starting with the detector to the right of the patient (and the x-ray source to the left of the patient). An imaging frequency of 10 Hz is assumed, resulting in 600 projections per scan.

The simulated projections are used for estimation of the Gaussian probability distribution with MLE, and the resulting Gaussian parameters are compared with the actual values of ($\mu_{LR}$, $\mu_{CC}$, $\mu_{AP}$), ($\sigma_{LR}$, $\sigma_{CC}$, $\sigma_{AP}$), and ($\rho_{LR-CC}$, $\rho_{LR-AP}$, $\rho_{CC-AP}$) as directly calculated from the actual 3D trajectory. The trajectories are estimated by use of the Gaussian distribution and compared with the actual trajectories for calculation of the root-mean-square (rms) error and maximum error for each trajectory.

Finally, to investigate potential improvements, ($\mu_{LR}$, $\mu_{CC}$, $\mu_{AP}$), ($\sigma_{LR}$, $\sigma_{CC}$, $\sigma_{AP}$), and ($\rho_{LR-CC}$, $\rho_{LR-AP}$, $\rho_{CC-AP}$) are recalculated directly from the estimated trajectories and again compared with the values for the actual trajectories.

The method is experimentally investigated by acquiring CBCT scans of a phantom on a 3D motion stage that reproduced two selected patient-measured trajectories: a typical lung tumor trajectory and a prostate trajectory with large motion in the axial plane. Before CBCT acquisition, the origin of the motion stage is calibrated such that a 1-mm-diameter spherical marker in the phantom coincided with the CBCT isocenter within 0.5 mm.

The CBCT scans are acquired with an On-Board Imager system mounted on a Trilogy linear accelerator (Varian Medical Systems, Palo Alto, Calif.). The scan duration is 60 sec during which approximately 640 projections are acquired over 360° with a frame rate of 10.7 Hz. The pixel length in the projection images is 0.388 mm at the detector and 0.259 mm at the isocenter. The projected position of the marker in the phantom is extracted automatically from each image by a research prototype version of the RPM-Fluoro application, version 0.7.10 (Varian Medical Systems). A calibration scan of the static phantom positioned with the marker in the isocenter of the CBCT system is used for correction of offsets and gantry-angle-dependent flex of the imager system. The projected position of the static marker is fitted to a sine function in the CC direction and a constant value in the direction perpendicular to the CC axis which are then subtracted from the experimentally obtained projections of the moving phantom.

The 3D trajectories are estimated from the extracted marker positions by the method of the current invention and compared with (1) the actual trajectories used to drive the motion stage and (2) the trajectories when estimated from simulated rather than experimental projections. These simulations are made with the same number of projections, acquisition times, and acquisition angles as in the experiments.

The uncertainties in this example included the accuracy of the motion stage positioning (submillimeter), the accuracy of the marker extraction (approximately 1 pixel=0.26 mm), and the residual error after correction for imager offsets and flex (subpixel).

In a retrospective study, the CBCT projections for a patient with two markers implanted in the pancreas are used to demonstrate clinical use of the method. The tumor trajectory is estimated from the extracted position of one marker in the projection images. For comparison with a true 3D measurement, the marker is delineated in each of 10 respiratory phases of a 4D CT scan of the patient by using a segmentation threshold of 2000 HU. The center-of-mass position of the delineated marker is compared with the 3D trajectory estimation from the CBCT projections. The 4D CT scan is acquired the same day as the CBCT scan.

The distribution of estimation errors for the mean position and standard deviation are presented in FIGS. 3a-3f and FIGS. 4a-4f. In the LR and AP directions, these distributions are somewhat broader for prostate than for thoracic/abdominal tumors. In the CC direction, both tumor sites show very small estimation errors. FIGS. 3a-3f show the distribution of errors in the estimated mean tumor position (a-c) for thoracic and abdominal tumors and (d-f) for prostate. Here, CBCT=cone-beam CT; CC=cranio-caudal; LR=left-right; AP=anterior-posterior.

FIGS. 5a-5d show the estimated motion correlation coefficients for different pairs of directions as function of the actual correlation coefficients. For thoracic/abdominal tumors, all three correlation coefficients are estimated (FIGS. 5a-5c), whereas only $\rho_{CC-AP}$ is estimated for prostate (FIG. 5d). The CC-AP prostate motion correlation is predominantly positive meaning that anterior prostate motion is often accompanied by cranial motion. Here, directions for thoracic/abdominal tumors are shown in FIG. 5a for LR-CC directions, FIG. 5b for LR-AP directions, FIG. 5c for CC-AP directions, and FIG. 5d for prostate in CC-AP directions. Further, CBCT=cone-beam CT; CC=cranio-caudal; LR=left-right; AP=anterior-posterior.

Figure 6:
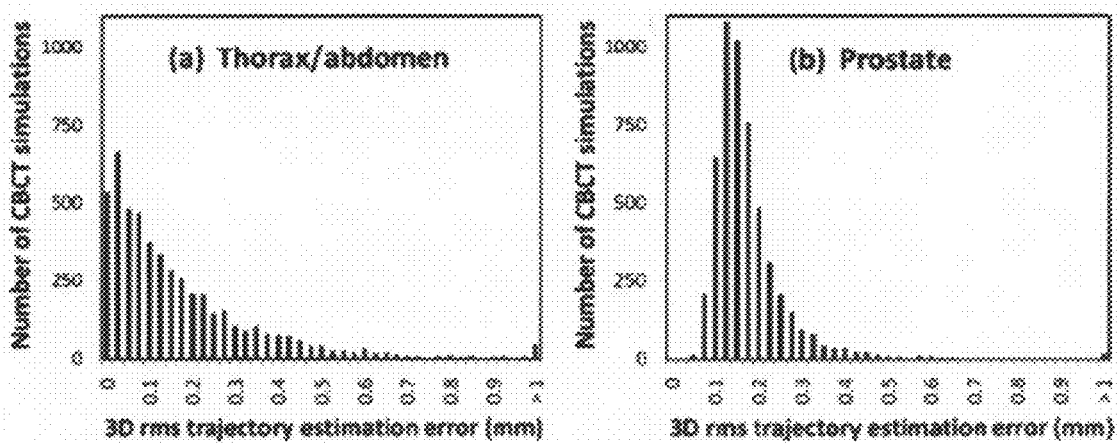
FIGS. 6a-6b show the distribution of 3D rms errors in the trajectory estimations according to the present invention.

The distribution of 3D rms errors in the trajectory estimations are shown in FIG. 6a-6b. The distribution are more narrow for prostate (FIG. 6b) with most 3D rms errors being FIG. 6. Distribution of errors in the estimated mean tumor position (a-c) for thoracic and abdominal tumors and (d-f) for prostate. CBCT=cone-beam CT; CC=cranio-caudal; LR = left-right; AP=anterior-posterior. Here, FIGS. 6a-6b show the distribution of three-dimensional (3D) root-mean-square (rms) errors in the estimated trajectories for FIG. 6a thoracic and abdominal tumors and FIG. 6b for prostate. CBCT=cone-beam CT.

Figure 7:
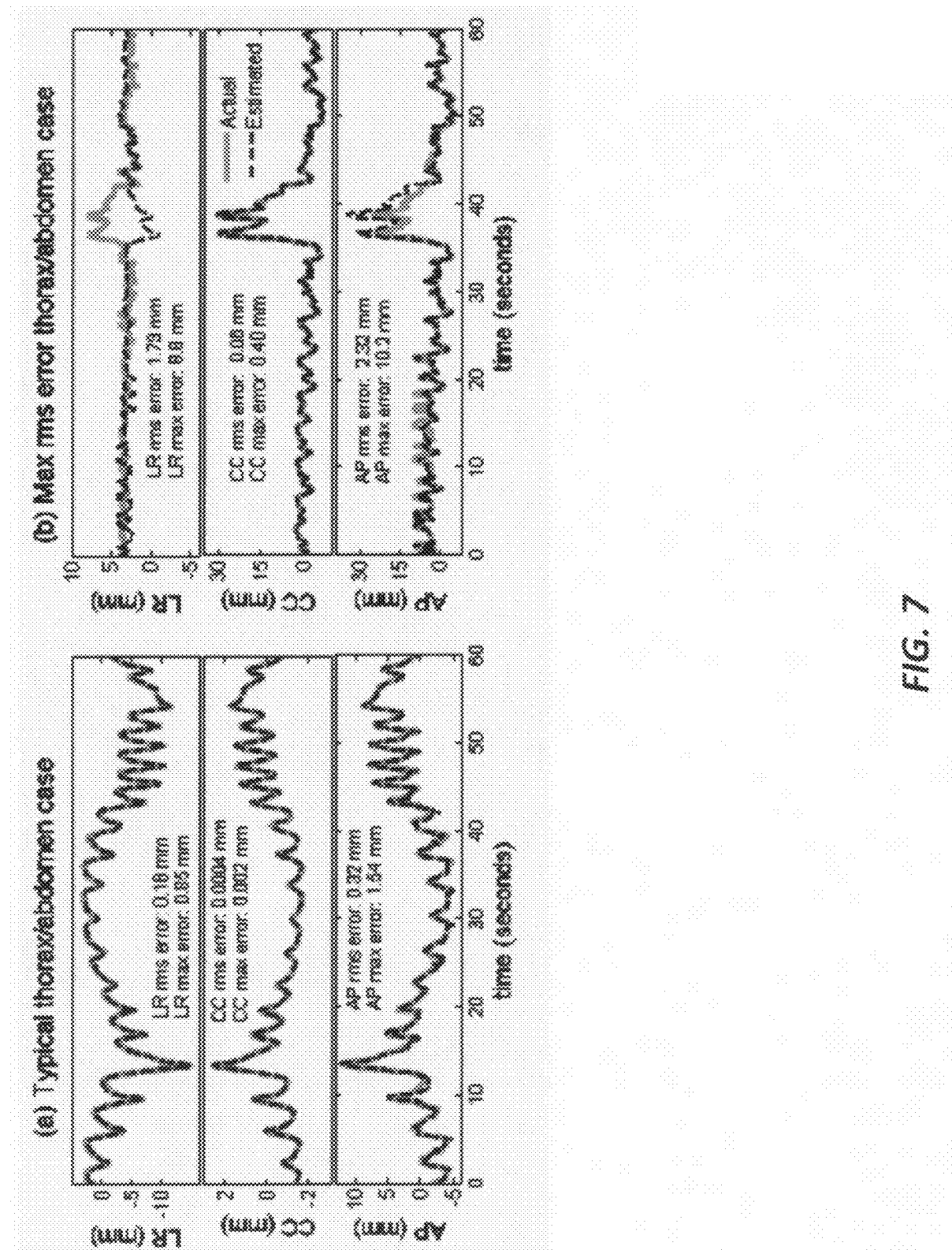
FIGS. 7a-7b show two examples of lung tumor trajectories as estimated from simulated cone-beam CT projections, according to the present invention.

FIG. 7a compares the estimated tumor trajectory with the actual trajectory for a typical thoracic tumor case. The figure presents the rms and maximum estimation errors in each direction. The trajectory with the largest vector rms estimation error (2.89 mm) is compared with the actual trajectory in FIG. 7b. Two examples of lung tumor trajectories as estimated from simulated cone-beam CT projections are shown, where in FIG. 7a Typical case is shown and in FIG. 7b the thoracic/abdominal case with largest root-mean square (rms) estimation error. The numbers present the rms error and maximum error for the estimated trajectory. CC=cranio-caudal; LR=left-right; AP=anterior-posterior. The large estimation error in the LR direction at approximately 40 sec resulted from fluctuating motion correlation during the CBCT acquisition.

Figure 8:
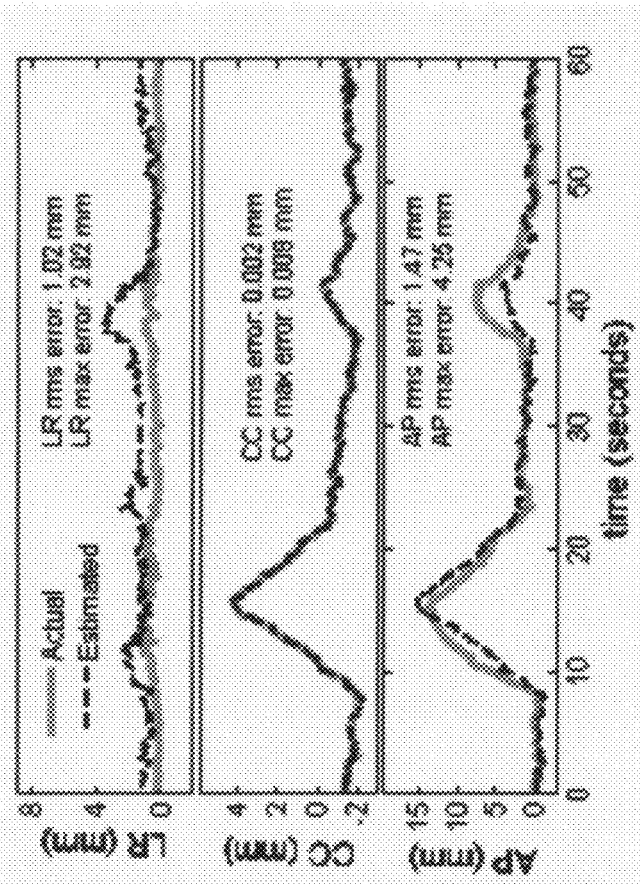
FIGS. 8a-8b show two examples of prostate trajectories as estimated from simulated cone-beam CT projections according to the present invention.
Figure 8:
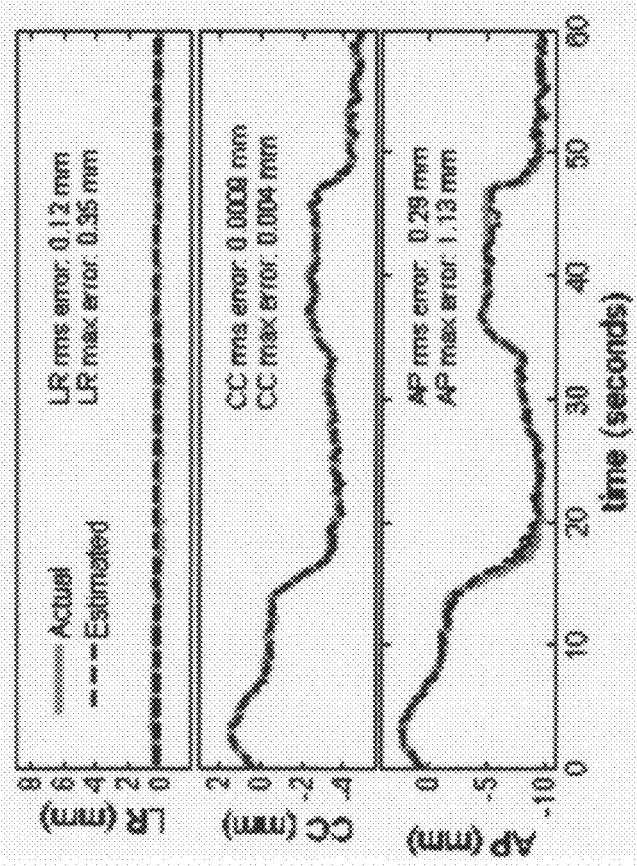

FIG. 8a shows the estimated trajectory for a representative prostate case and a prostate case with large estimation errors. Here, FIGS. 8a-8b show two examples of prostate trajectories as estimated from simulated cone-beam CT projections, where FIG. 8a shows a typical case and FIG. 8b shows a case with large estimation errors. The numbers present the root-mean-square (rms) error and maximum error for the estimated trajectory. CC=cranio-caudal; LR=left-right; AP=anterior-posterior.

Recalculation of ($\mu_{LR}$, $\mu_{CC}$, $\mu_{AP}$), ($\sigma_{LR}$, $\sigma_{CC}$, $\sigma_{AP}$), and ($\rho$LR-CC, $\rho$LR-AP, $\rho$CC-AP) directly from the estimated trajectories only improved the accuracy in the CC direction, for which MLE already resulted in very high accuracies, as seen in. For thoracic/abdominal tumors, the recalculation reduced the maximum error of $\mu_{CC}$ and $\sigma_{CC}$ to 0.01 mm and 0.05 mm, respectively. For prostate, the maximum errors were reduced to 0.004 mm ($\mu_{CC}$) and 0.007 mm ($\sigma_{CC}$).

Figure 9:
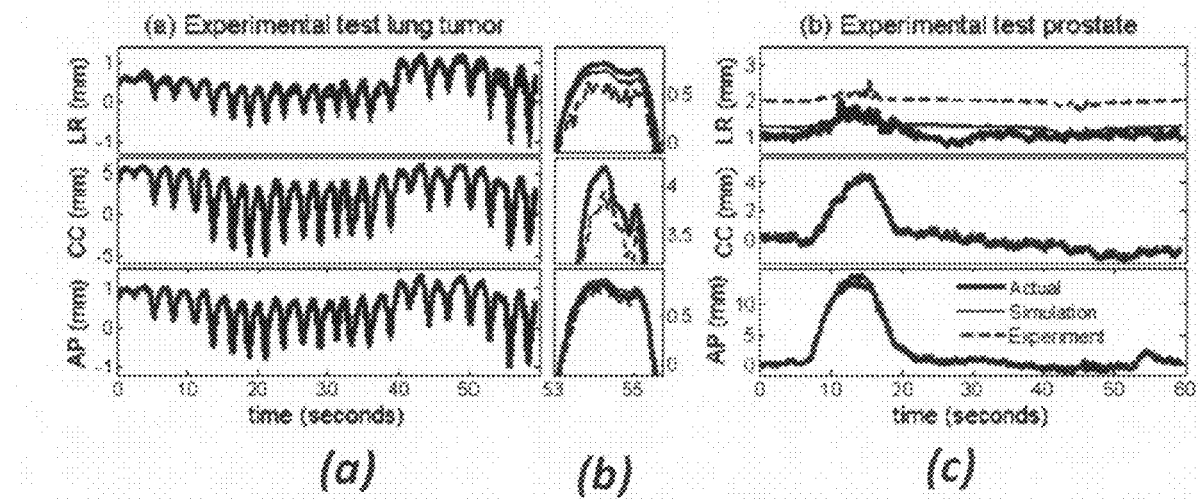
FIGS. 9a-9c show experimentally investigated trajectories according to the present invention.

The experimentally investigated trajectories are shown in FIGS. 9a-9b. Each graph compares the actual phantom trajectory with the trajectory estimated both from the extracted marker position in the CBCT projections and from simulated projections. The difference between each trajectory pair can be characterized by its mean value and its standard deviation, which represent a systematic difference and a random difference, respectively. In the experimental investigation of the prostate trajectory, the tabletop was unintentionally shifted away from the fine adjusted isocenter position and back again to the same lateral couch readout before CBCT acquisition. Failure to reach exactly the same position probably caused the relatively large systematic difference between experiment and simulation in the LR direction (FIG. 9b). FIGS. 9a-9b show the trajectory estimated from experimental cone-beam CT projections, actual trajectory fed into the motion stage, and trajectory estimated from simulated projections for FIG. 9a lung tumor and FIG. 9b prostate. The right side of FIG. 9a shows one breathing cycle. Positive values correspond to left, cranial, or anterior directions. CC =cranio-caudal; LR=left-right; AP=anterior-posterior.

Figure 10:
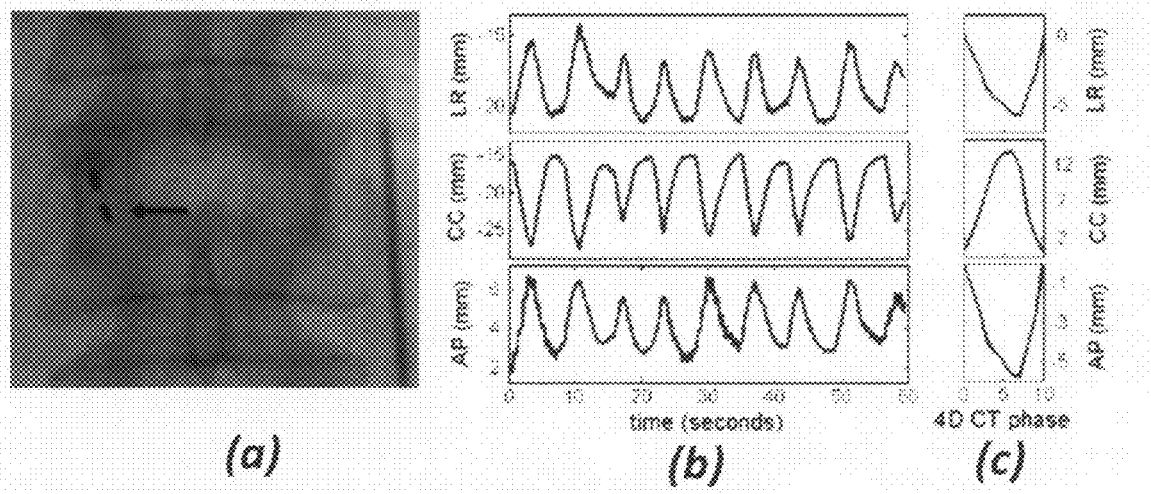
FIGS. 10a-10c shows an anterior projection from the CBCT projection data set for a pancreas cancer patient (left), the estimated pancreas trajectory from the entire CBCT projection data set according to the present invention (middle), and the pancreas trajectory determined from a 4D CT scan (right).

FIGS. 10a-10c show an anterior projection from the CBCT projection data set for a pancreas cancer patient. The projected position of the most caudal marker is extracted from each projection and used for estimation of the trajectory shown in FIG. 10b. FIG. 10c shows the marker position in the 4D CT scan with the same vertical scale as used for the CBCT estimated trajectory. FIG. 10a shows an anterior cone-beam CT projection of a patient with two fiducial markers in the pancreas. The position of the caudal marker (arrow) was extracted from all projections and used for estimation of the trajectory shown in FIG. 10b. FIG. 10c shows marker position in the 10 respiratory phases of a four-dimensional (4D) CT scan. CC=cranio-caudal; LR=left-right; AP=anterior-posterior.

Figure 3:
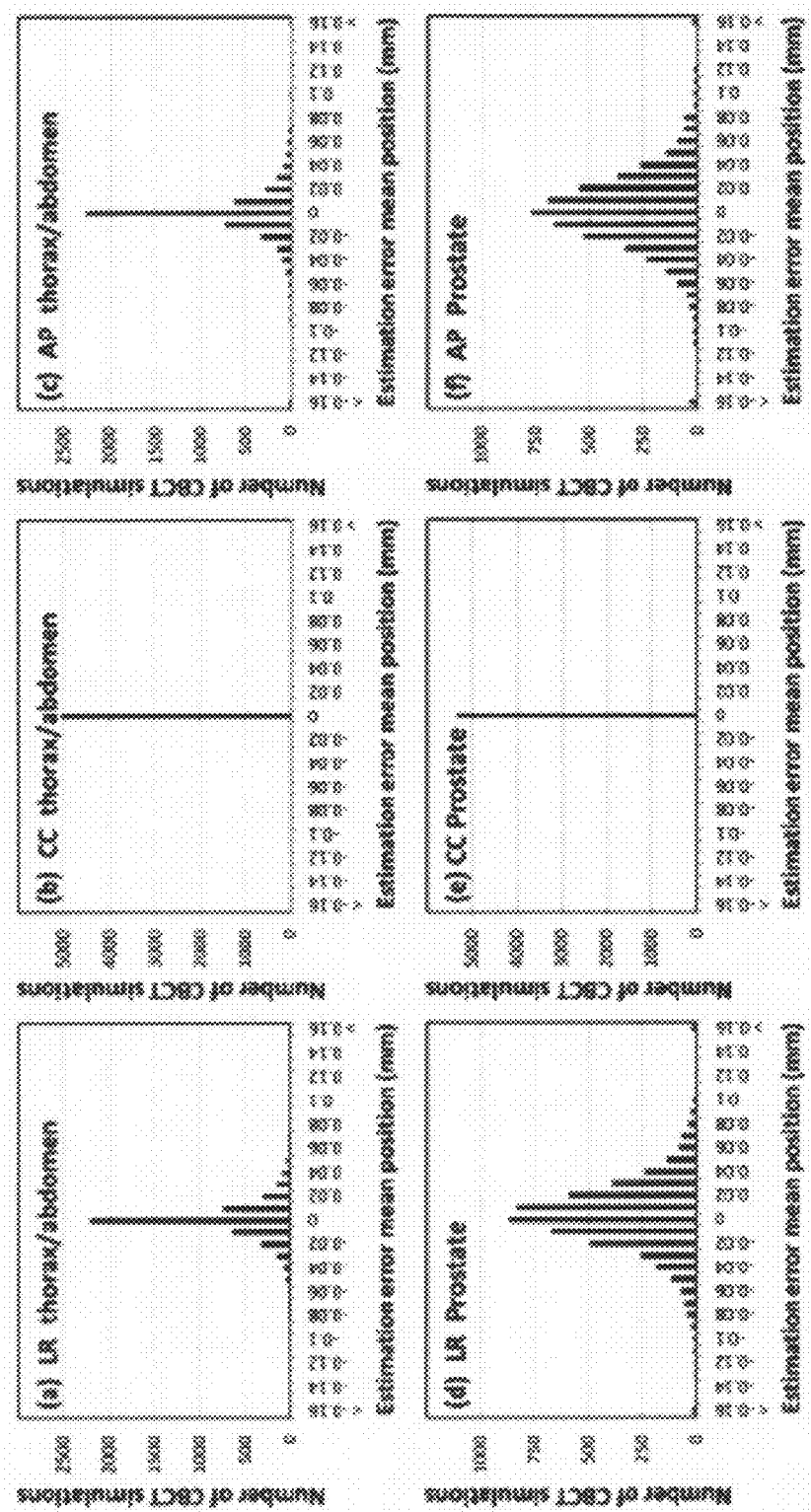
FIGS. 3-4 show the distribution of estimation errors for the mean position and standard deviation, according to the present invention.
Figure 4:
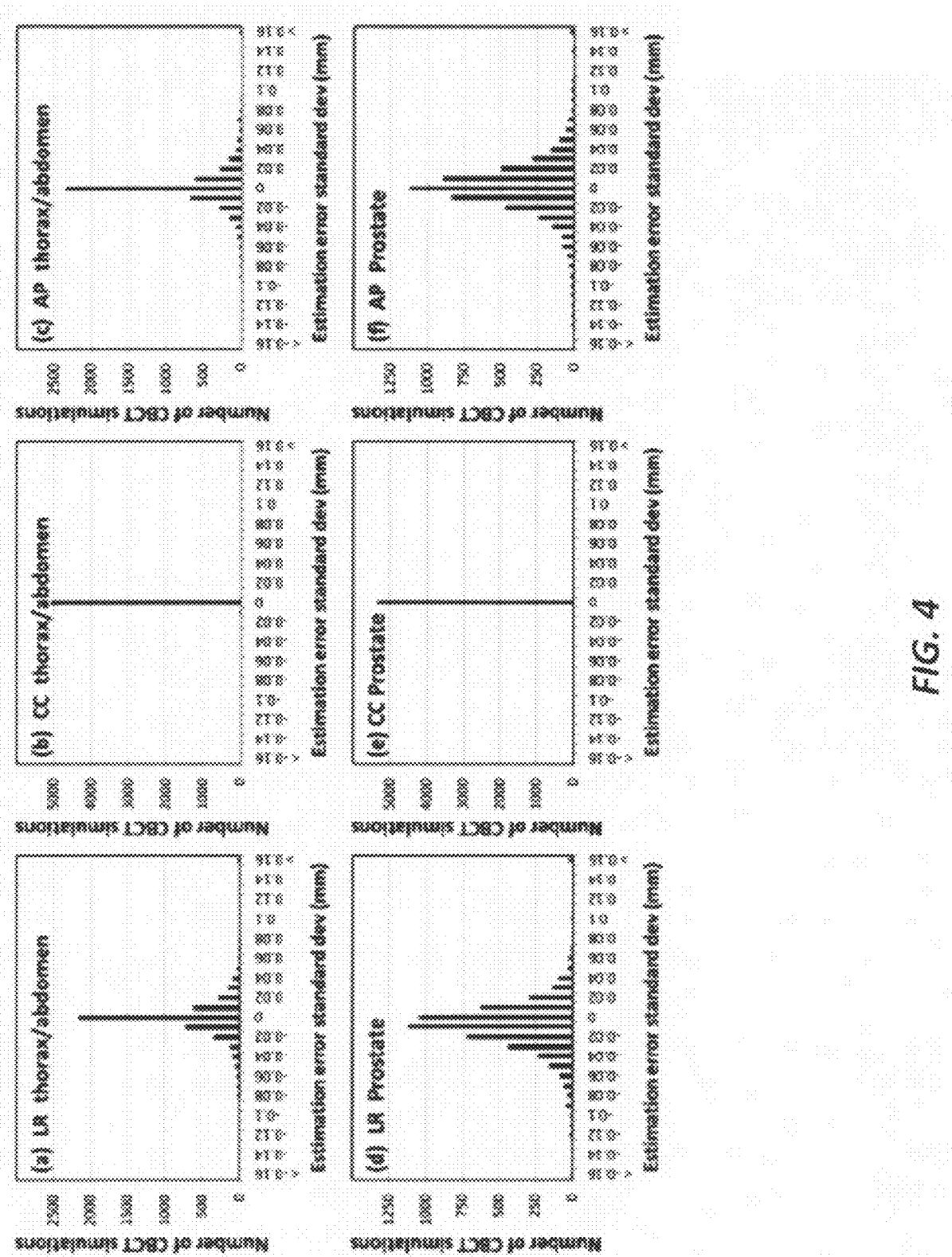

The invention for assessment of tumor motion from CBCT projections lead to very accurate estimations of the mean and standard deviation of the tumor position (FIG. 3 and FIG. 4). In more than 10,000 CBCT simulations of patient-measured tumor trajectories, no 3D error in the mean position estimation exceeded 1 mm, and no error in any standard deviation component exceeded 1.5 mm. The method according to the invention also provided good estimations of the tumor trajectories with a mean 3D rms error less than 0.2 mm for both tumor sites. The experimental investigation demonstrated that the high accuracy anticipated by the simulations is not notably degraded in a practical setting by the additional experimental inaccuracies. It paves the road for clinical application as demonstrated by the clinical case study.

In the method of the present study, the full 2D information of all projections is readily used in the MLE estimation of the Gaussian probability density. The largest errors were found in the LR and AP directions, that is, in the axial plane where the position component along the imager axis is unresolved and therefore not possible to determine exactly. In contrast, the CC position is resolved for all imaging angles, and the only CC error contribution is magnification errors resulting from inaccurate estimations of the unresolved position. A wrong estimation by 13.6 mm (the largest error in this study) leads to an error in the CC position of only 1.4%. Hence, the estimation of the mean position and standard deviation in the CC direction was very accurate (FIGS. 3 and FIGS. 4).

Figure 5:
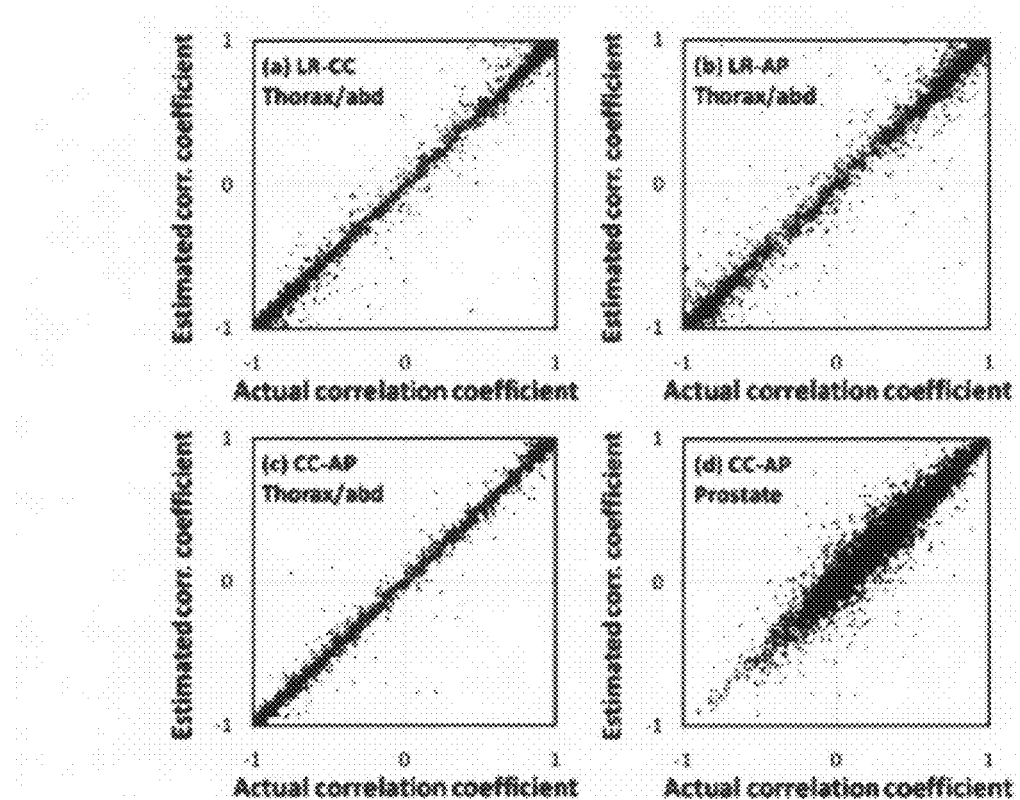
FIGS. 5a-5d show the estimated motion correlation coefficients for different pairs of directions as function of the actual correlation coefficients, according to the present invention.

The MLE method in general provided good estimates of the motion correlation (FIGS. 5). The LR-AP motion correlation of thoracic/abdominal tumors was estimated slightly less accurately than the correlations involving CC motion, which is to be expected because the LR and AP positions are never resolved simultaneously during CBCT acquisition. In general, the motion correlation is considerably larger for thoracic and abdominal tumors (FIGS. 5a-5c) than for prostate (FIG. 5d), which is presumably a major reason for the better estimations of mean position and standard deviation for thoracic and abdominal tumors (narrower distributions in the upper row in FIGS. 3 and FIGS. 4).

Most tumor trajectories are well estimated. In 99.1% of the thoracic/abdominal cases and in 99.7% of the prostate cases, the 3D rms error of the estimated trajectory is less than 1 mm. Similar to the mean positions and standard deviations, the trajectories are estimated markedly better in the CC direction than in the axial plane.

FIGS. 7b and 8b illustrate that even in cases with large trajectory estimation errors, the LR position is estimated correctly around 15 sec and 45 sec, which corresponded to posterior and anterior imaging angles, respectively. Similarly, the AP position is always estimated accurately around 0, 30, and 60 sec (left, right, and left imaging). In general, the correlation between CC motion and either LR or AP motion will primarily be established from projections in certain gantry-angle intervals (in which the LR/AP motion in question is resolved) and used for trajectory estimation in perpendicular angle intervals (in which the LR/AP motion is unresolved). Therefore, the trajectory estimation method can be vulnerable to fluctuating motion correlations during the CBCT scan.

The trajectory in FIG. 7b illustrates this point. Here, the positive LR around 40 sec is wrongly estimated as negative displacement. The $\rho_{LR-CC}$ estimation is mainly based on the time intervals around 15 and 45 sec, where both LR and CC motion are resolved. In this particular case, most motion occurred in the second of these intervals (45 sec), where the LR motion is positive and the CC motion is negative. Therefore, $\rho_{LR-CC}$ is estimated as being negative. When a large positive CC displacement occurred around 40 sec, the unresolved LR displacement is thus estimated wrongly as negative LR displacement. This example illustrates that the trajectory estimation can be less accurate with unstable motion correlation during the CBCT scan.

In comparison with thoracic/abdominal tumors, the mean position errors and standard deviation errors for prostate had broader distributions (FIGS. 3a-3f and FIGS. 4a-4f). Furthermore, the motion correlation for prostate is in general weaker (FIG. 5d), and $\rho_{PLR-CC}$ and $\rho_{PLR-AP}$ are not even estimated for prostate. As a result, less accurate trajectory estimations should be expected for prostate, but this is not reflected by the mean and maximum errors. A lower accuracy for the prostate trajectory is, however, revealed by the absence of very accurate prostate trajectory estimations with rms errors below 0.05 mm. Such cases constituted only 0.1% of the prostate cases (FIG. 6b) in contrast to nearly 30% for thoracic/abdominal tumors (FIG. 6a). Also apparent from FIGS. 6 is a smaller tail toward large errors in the prostate error distribution (most likely because of the generally smaller motion magnitude for prostate), which results in mean and maximum errors that are similar to those of thoracic/abdominal tumors.

The results of the example provided are summarized in FIGS. 9a-9b. The difference between the experimentally derived and actual phantom trajectories includes imperfect phantom alignment with the isocenter. This contribution will show up as a systematic shift (a finite mean error), which is actually the main contributor to the observed difference. Except for some systematic shifts, there is close agreement between the trajectories estimated from experimental projections and from simulated projections (FIGS. 9a-9b). It indicates that the errors introduced in the experimental setting will not notably influence the conclusions from the simulation study. The example thus serves as a link to clinical applications.

In the clinical case study (FIGS. 10a-10c), the accuracy of the trajectory estimation is unknown because the actual tumor motion is unknown. However, the good results in the simulations and experimental study indicate that the estimated tumor trajectory is very close to the actual tumor motion. This is supported by the 4D CT scan (FIG. 10c), which showed similar motion magnitude and motion correlation (positive CC motion correlated with negative LR and AP motion).

The probability-based method for 3D target position estimation from 2D projections described above, includes finite target mean positions. Restating, a target is projected into a point on the imager it is known to be located on the ray line that connects this point and the focus point of the imager system. In order to estimate the target position along this line, a 3D Gaussian PDF is assumed for the spatial target position. As a consequence the 1D probability density along the ray line is also Gaussian, and its mean position $\mu$ can be calculated from the 3D PDF. The unknown target position along the ray line (and thus the 3D target position) is then simply estimated as the mean position $\mu$. Equation (A.9) below gives an analytical expression for $\mu$ in terms of the 3D PDF. The 3D PDF needed for calculation of $\mu$ is not known, but it can be estimated from a series of projection images by maximum likelihood estimation (MLE). In this approach, the unknown parameters that define the PDF are selected such that the total likelihood of the observed target projections under consideration is maximized. The objective function to be minimized in this optimization problem can be expressed as a sum:

$$F_{MLE} = \sum_i f_{MLE,i} \quad (1)$$

The sum includes a contribution $f_{MLE}$, i for each image i considered for the PDF estimation. An analytical expression for $f_{MLE}$, i is given below. When the PDF that minimizes $F_{MLE}$ has been found, it can be used for estimation of the 3D target position as described above. The implementation of the MLE optimization found that prostate trajectory estimations are generally better if left-right (LR) prostate motion is assumed not to correlate with anterior-posterior (AP) or cranio-caudal (CC) motion. These MLE optimizations are made with this assumption for the following aspect of the invention.

The invention provides important information for motion-inclusive, respiratory-gated, and tumor-tracking image-guided radiotherapy. With motion-inclusive radiotherapy, in which intrafraction tumor motion is accounted for by margins, an accurate estimation of the mean tumor position is essential for minimizing systematic errors. Because the standard deviation and tumor motion correlation allow calculation of appropriate margins that account for both motion magnitude and directionality, these quantities are valuable in evaluating and verifying margins for respiratory motion. They could be used for adaptation of margins or selection of motion management strategy (e.g., motion-inclusive radiotherapy or gating) for individual treatment sessions. For respiratory gating, the estimated 3D trajectory allows evaluation of respiratory regularity before treatment and individualization of the gating window to accommodate daily baseline shifts.

For tumor tracking, using the invention as described to this point needs modification of real-time trajectory estimation because it is retrospective and requires two parses of all CBCT projections: a first parse for estimating the probability density and a second for estimating the trajectory. In an online implementation (e.g., for tracking during arc treatment), the probability density could be estimated either by a preceding CBCT scan or by use of the subset of projections recorded up to the present point in time The current invention further provides a method of trajectory estimation from CBCT projections in a retrospective manner since the PDF is estimated from all projections in the CBCT series. Such retrospective estimation is not directly applicable for prospective real-time target position monitoring during an arc treatment where only projections acquired up to the actual point in time would be available for the estimation. The present aspect extends the retrospective trajectory estimation method to prospective real-time trajectory estimation.

According to the current invention, image-guided real-time prostate position estimation is illustrated by simulating x-ray imaging with a single imager during arc therapy. The simulations are based on 548 prostate trajectories recorded with implanted electromagnetic transponders for 17 patients treated in supine position at MD Anderson Cancer Center Orlando. Prostate (surrogate) visibility on all projection images is assumed. Imaging is simulated by projecting the 3D prostate position onto a rotating flat panel detector whenever an image was assumed to be acquired.

Figure 11:
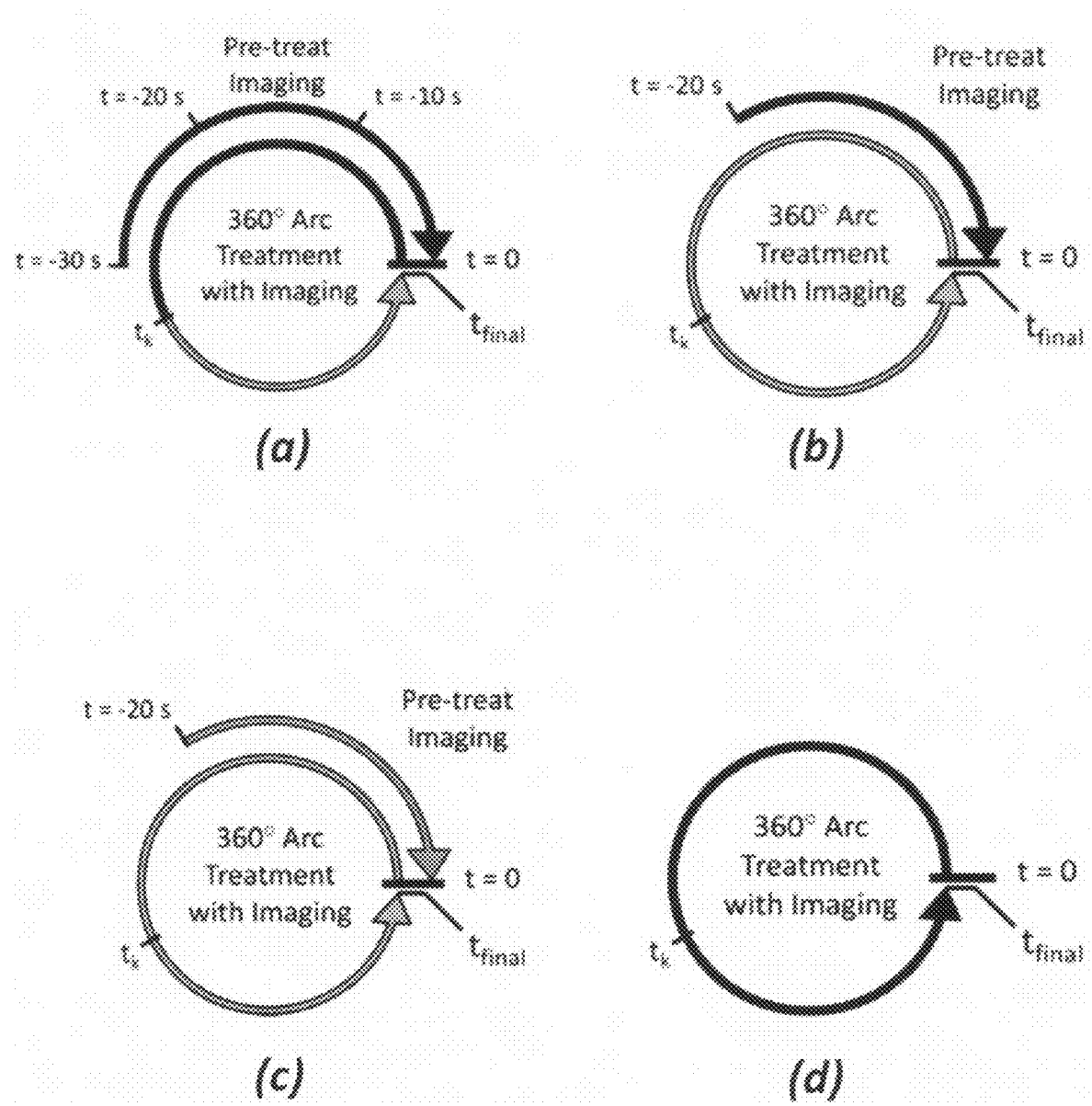
FIGS. 11a-11d. show different scenarios for real-time establishment of the PDF for prostate position estimation during arc therapy according to the present invention.

FIGS. 11a-11c show three different scenarios for real-time establishment of the PDF for prostate position estimation during arc therapy. The inner circle in each figure shows the position of the imager source during the arc treatments. It starts at t=0 on the left side of a head-first supine patient and performs a full 360° rotation ending at time $t_{final}$ (60 sec, 120 sec or 180 sec). The outer, arced arrow represents pre-treatment imaging for 10 sec, 20 sec or 30 sec. At time $t_k$, the 3D prostate position is estimated using a PDF based on the images indicated by the black part of the arced arrows. The PDF in FIG. 11a is based on all images acquired up to $t_k$, in FIG. 11b is based on pre-treatment images and in FIG. 11c is a population-based PDF, where the pre-treatment images are used for estimation of the mean target position, only. For comparison, the target trajectory is also estimated retrospectively with a PDF based on all intra-treatment images in FIG. 11d.

The arc treatment is performed immediately after the pre-treatment imaging with a single 360° counter-clockwise gantry rotation of either 1, 2 or 3 min duration. Simulations are made with constant imaging frequencies of 0.5, 1, 2 and 5 Hz for both pre-treatment and intra-treatment imaging. Whenever an image is acquired during treatment, the 3D prostate position is estimated from the projected prostate position in this image and one of the following PDFs for real-time position estimation.

(1) Dynamically updated PDF estimated from the present image and all previously acquired images (FIG. 11a).
(2) Static individualized PDF estimated from the pre-treatment images only (FIG. 11b).
(3) Static population-based PDF determined from all available prostate trajectories as follows.

All trajectories are divided into 1 min segments which are individually shifted to obtain zero mean displacement. All segments are then added together to a single trajectory for which the covariance matrix is calculated (equation (A.1)) and used for establishment of the 3D PDF (equation (A.2)). The mean position of the PDF is estimated individually for each simulated treatment from pre-treatment images acquired over 20 s (FIG. 11c).

For the simulations, all 548 prostate trajectories are divided into segments with durations of either 1, 2 or 3 min. The total number of 1, 2 and 3 min trajectory segments for simulation was 4728, 2227 and 1390, respectively. The mean motion ranges are 0.7 mm (LR), 1.6 mm (CC) and 1.9 mm (AP) for the 1 min segments; 0.8 mm (LR), 2.1 mm (CC) and 2.4 mm (AP) for the 2 min segments; and 0.9 mm (LR), 2.5 mm (CC)

and 2.9 mm (AP) for the 3 min segments. The maximum motion range is 3.7 mm (LR), 19.7 mm (CC) and 19.1 mm (AP) both for the 1-min, 2-min, and 3-min segments.

For each simulation, the difference between the estimated 3D prostate position and the actual position is calculated for all intra-treatment images. The root mean square (RMS) and maximum value of this estimation error are then calculated for each treatment.

For comparison, the position estimation error is also calculated for three scenarios that do not represent 3D real-time trajectory estimation. These scenarios are as follows.
(1) Probability-based 3D trajectory estimation with a PDF that is based on all intra-treatment images (FIG. 11d). This estimation is retrospective rather than real time. It can be used to estimate the target trajectory from a CBCT scan.
(2) No estimation of the unresolved motion. For each image, the prostate position in the unresolved direction perpendicular to the imager was assumed to equal the position in this direction at treatment start. This scenario illustrates the magnitude of the unresolved intrafraction prostate motion and thus the gain that can be obtained by estimation of this motion.
(3) No estimation of the intrafraction motion. This scenario corresponds to perfect localization at treatment onset without further intra-treatment localization. It illustrates the magnitude of the intrafraction prostate motion.

Table 1 summarizes the parameters of the simulations made in this study including the resulting number of images. The first simulation in this table (20 sec pre-treatment imaging, 5 Hz, 1 min treatment with a dynamic PDF) is chosen as a standard. In all other simulations, only one parameter is altered from this standard setting. Parameters that differ from the standard parameters (listed in the first row) are written in bold. The last three rows are the reference scenarios that do not represent real-time 3D position estimation. Pre-treatment Image Treatment No of images Figure and PDF imaging frequency duration (pre+intratreat) table no.

TABLE 1

| PDF | Pre-treatment imaging | Image frequency | Treatment duration | No of images (pre + intratreat) |
|---|---|---|---|---|
| Dynamic | 20 s | 5 Hz | 1 min | 100 + 300 |
| Static individualized | 20 s | 5 Hz | 1 min | 100 + 300 |
| Static population-based | 20 s | 5 Hz | 1 min | 100 + 300 |
| Dynamic | 10 s | 5 Hz | 1 min | 50 + 300 |
| Dynamic | 30 s | 5 Hz | 1 min | 150 + 300 |
| Dynamic | 20 s | 0.5 Hz | 1 min | 10 + 30 |
| Dynamic | 20 s | 1 Hz | 1 min | 20 + 60 |
| Dynamic | 20 s | 2 Hz | 1 min | 40 + 120 |
| Dynamic | 20 s | 5 Hz | 2 min | 100 + 600 |
| Dynamic | 20 s | 5 Hz | 3 min | 100 + 900 |
| Retrospective | 0 s | 5 Hz | 1 min | 0 + 300 |
| None (no estimation of unresolved) | 0 s | 5 Hz | 1 min | 2 + 300 |
| None (no motion estimation) | 0 s | — | 1 min | 2 + 0 |

The relationship between the objective function contribution $f_{MLE}$ and the estimation error of an image is established for the standard real-time trajectory estimation (first row in Table 1) as follows: for each intrafraction image, the objective function contribution $f_{MLE}$ and the magnitude of the 3D position estimation error are recorded during the simulations. All images are then sorted according to their value of $f_{MLE}$ and grouped into 200 bins that each contained 0.5% of the images (7092 images). The 7092 images with the lowest $f_{MLE}$ values are grouped in the first bin. The 7092 images with the next-lowest $f_{MLE}$ values are grouped in the second bin and so on. Bin number 200 included the 7092 images with the highest $f_{MLE}$ values. For each bin, the mean $f_{MLE}$ value is calculated and used to represent the bin.

Next, the distribution of position estimation errors is established for the first bin. For this group of images, the RMS error is calculated and the 95th percentile error, the 99th percentile error and the maximum error are recorded. Here, the 95th and 99th percentile errors are defined as the estimation errors that are not exceeded for 95% and 99% of the images in the bin, respectively. This procedure is repeated for all 200 bins and it resulted in the RMS error, the 95th and 99th percentile errors, and the maximum error as a function of the bin number and thus as a function of $f_{MLE}$.

Figure 12:
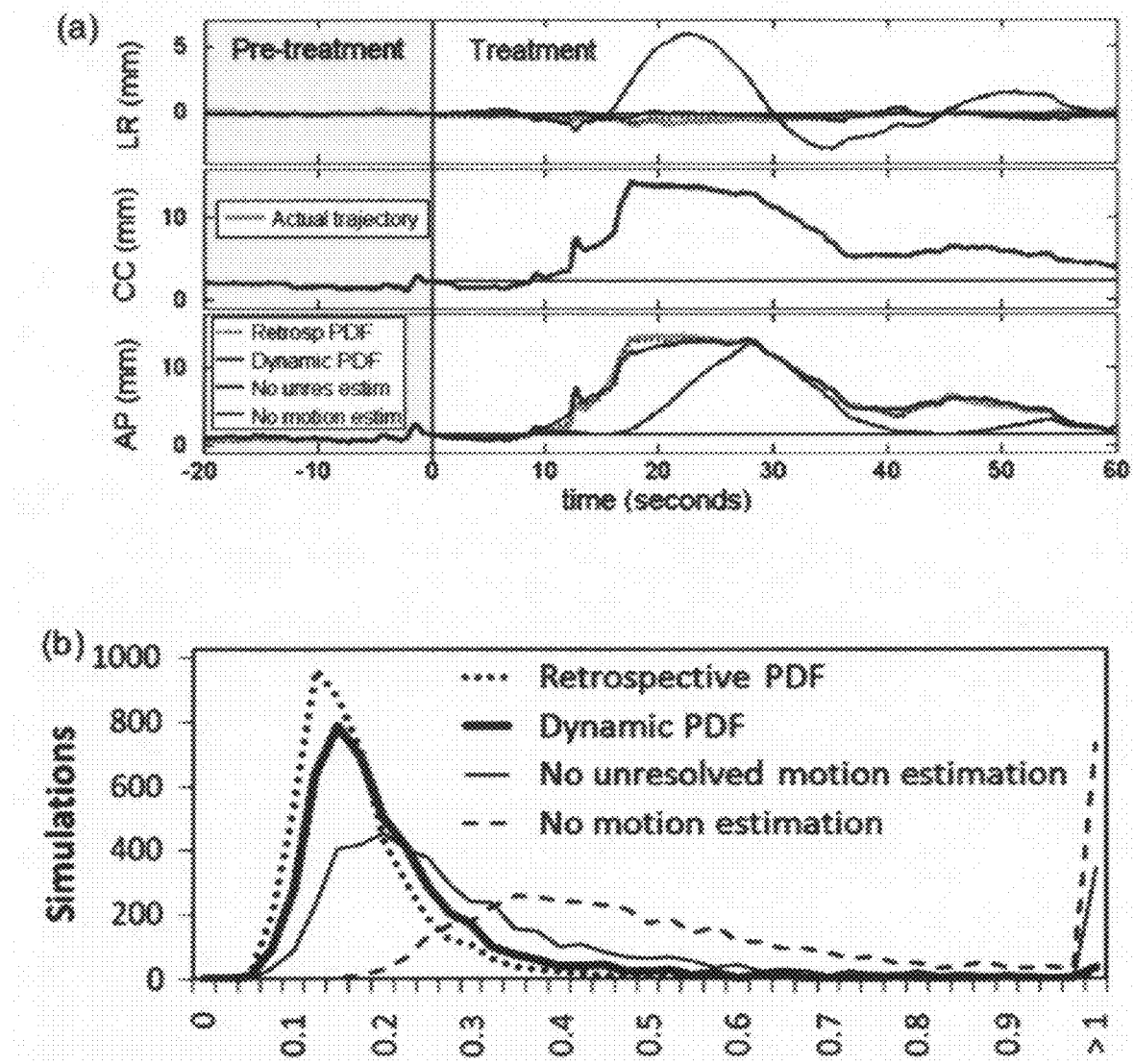
FIGS. 12a-b show a comparison of real-time 3D estimation with the three reference scenarios that do not represent 3D real-time trajectory estimation, and the corresponding distributions of 3D RMS errors, according to the present invention.

FIGS. 12a-12b compare real-time 3D estimation with the three reference scenarios that do not represent 3D real-time trajectory estimation. FIG. 12a shows a prostate trajectory and estimation hereof in either real time (with the standard parameters defined in the first row of table 4) or retrospectively (FIG. 11d scenario), with no estimation of the unresolved motion and no intrafraction motion estimation at all. FIG. 12a shows in the CC direction, the three methods with intra-treatment imaging are virtually indistinguishable. FIG. 12b shows the distribution of vector RMS errors in the trajectory estimations for all simulations with the retrospective PDF, with the real-time dynamic PDF, with no estimation of the unresolved motion and with no intra-treatment motion estimation.

All three scenarios with intrafraction motion estimation resulted in good estimations of the CC motion, which is resolved in all images. The assumption of no motion in the unresolved direction resulted in considerable errors in the LR and AP directions due to the large AP prostate motion that started 10 sec into the treatment. Although the real-time estimation was able to account for most of the AP motion, it was slightly inferior to the retrospective estimation. As seen by the distributions of 3D RMS estimation errors in FIG. 12b and the summarizing quantities in Table 2, these characteristics were quite general. Although the real-time estimation was not quite as good as the retrospective estimation, it lead to a dramatic reduction in RMS errors above 1 mm as compared to no estimation of the unresolved motion.

Table 2 shows RMS errors with real-time 3D trajectory estimation, retrospective trajectory estimation, no estimation of the unresolved motion and no estimation at all of intra-treatment motion. Mean and maximum of RMS error and percentage of trajectories with vector RMS errors exceeding 1 mm are shown.

TABLE 2

|  | Mean RMS error (mm) | | | | Maximum RMS error (mm) | | | | |
|---|---|---|---|---|---|---|---|---|---|
|  | LR | CC | AP | 3D | LR | CC | AP | 3D | >1 mm |
| Real-time PDF | 0.13 | 0.0003 | 0.18 | 0.22 | 2.6 | 0.03 | 3.7 | 4.5 | 0.8 |
| Retrospective PDF | 0.10 | 0.0002 | 0.14 | 0.18 | 1.2 | 0.01 | 1.7 | 1.9 | 0.3 |

TABLE 2-continued

|  | Mean RMS error (mm) | | | | Maximum RMS error (mm) | | | | |
| --- | --- | --- | --- | --- | --- | --- | --- | --- | --- |
|  | LR | CC | AP | 3D | LR | CC | AP | 3D | >1 mm |
| No estimation of unresolved | 0.24 | 0.0008 | 0.35 | 0.43 | 5.4 | 0.09 | 9.7 | 11.1 | 7.4 |
| No motion estimation | 0.18 | 0.46 | 0.56 | 0.79 | 2.0 | 14.5 | 14.6 | 20.6 | 15.5 |

Figure 13:
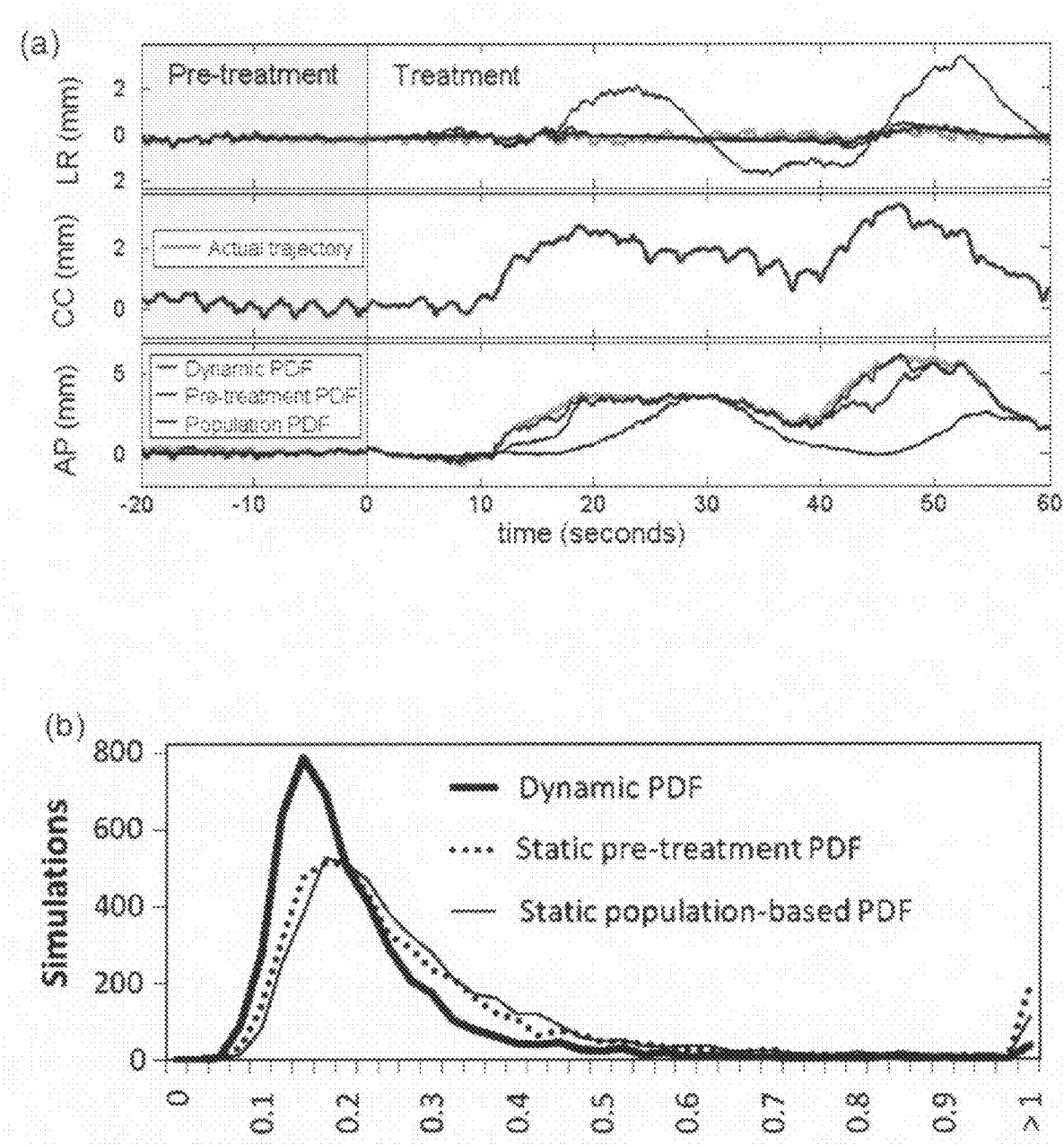
FIGS. 13a-13b show a comparison of real-time trajectory estimation with pre-treatment imaging durations of 10 sec, 20 sec, and 30 sec, and the corresponding distributions of 3D RMS errors, according to the present invention.

FIG. 13a gives an example of real-time trajectory estimation with the dynamic PDF and with static PDFs determined either from 20 sec pre-treatment imaging or as the population average (FIGS. 11a-11c). In this particular case, the pre-treatment imaging period did not involve large prostate motion. As a result, the PDF estimated from pre-treatment images failed completely in estimating the prostate motion during treatment. The population-based PDF was considerably better and only slightly inferior to the dynamically updated PDF.

FIG. 13b shows the distributions of 3D RMS estimation errors for all simulations with dynamic and static PDFs and Table 3 summarizes the mean and maximum values and the percentages of trajectories with 3D RMS errors larger than 1 mm. The dynamically updated PDF is clearly better than both static PDFs. While the static pre-treatment PDF is slightly better than the population PDF for the majority of trajectories, it also has a larger portion of poor estimations with 3D RMS errors larger than 1 mm.

TABLE 3

| PDF | Mean RMS error (mm) | | | | Maximum RMS error (mm) | | | | |
| --- | --- | --- | --- | --- | --- | --- | --- | --- | --- |
|  | LR | CC | AP | 3D | LR | CC | AP | 3D | >1 mm |
| Dynamic | 0.13 | 0.0003 | 0.18 | 0.22 | 2.6 | 0.03 | 3.7 | 4.5 | 0.8 |
| Pre-imaging, static | 0.18 | 0.0006 | 0.28 | 0.34 | 3.6 | 0.14 | 28 | 28 | 4.0 |
| Population, static | 0.16 | 0.0004 | 0.26 | 0.31 | 1.7 | 0.01 | 3.2 | 3.6 | 2.3 |

Figure 14:
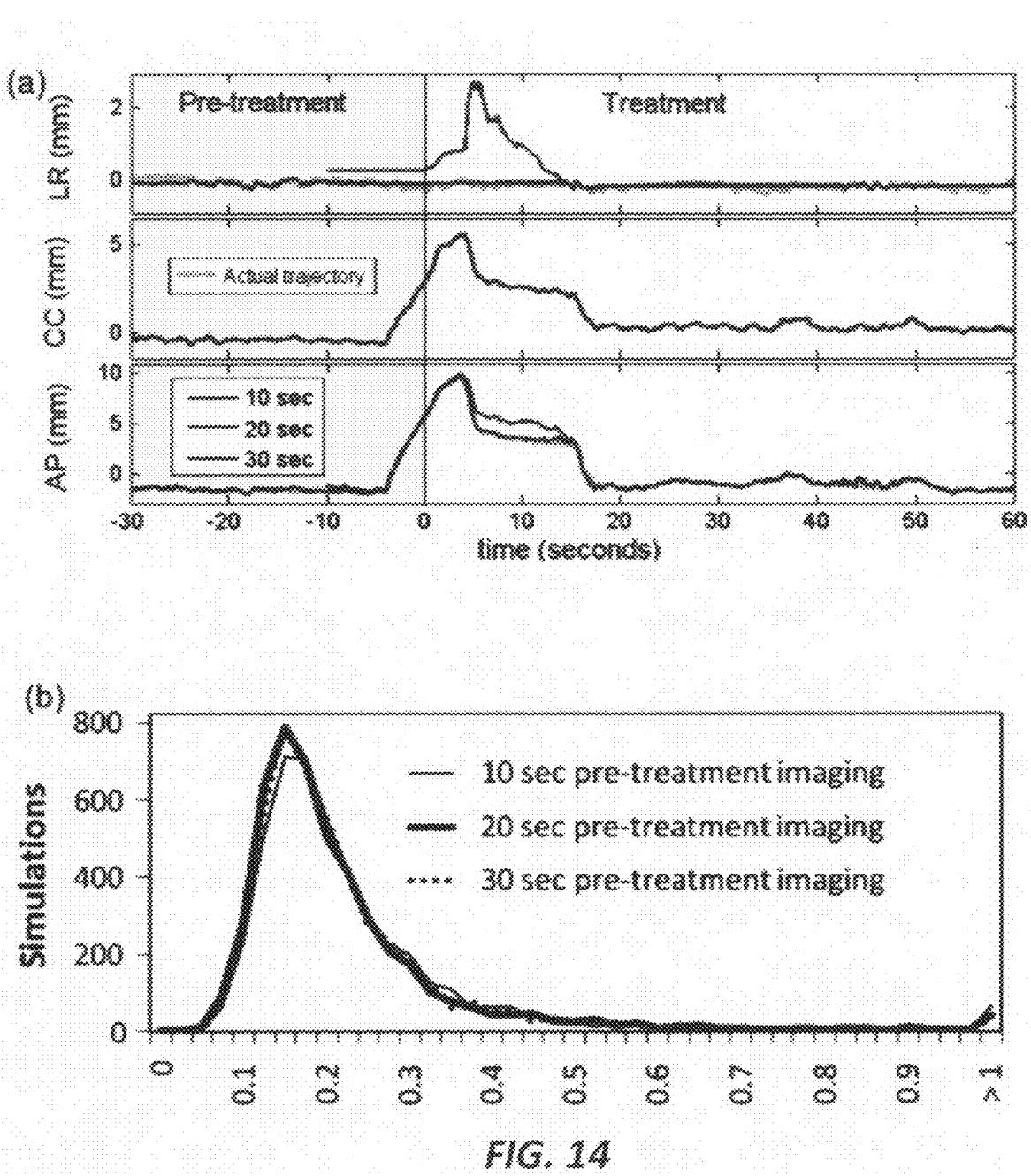
FIGS. 14a-14b show an example of real-time trajectory estimation with the dynamic PDF and with static PDFs, according to the present invention.

The purpose of the pre-treatment imaging is to establish an initial PDF for prostate position estimation right from the treatment onset. FIG. 14a shows an example of real-time position estimation with the dynamic PDF and pre-treatment imaging durations of 10 sec, 20 sec and 30 sec. For this case, a pre-treatment imaging of 10 sec is markedly inferior to 20 sec and 30 sec in the LR and AP directions respectively. This is mainly a result of an inaccurate estimation of the LR prostate position (see LR estimation in the upper part of FIG. 14a) caused by the lack of vertical pre-treatment images for the PDF estimation. The pre-treatment images for 10 sec acquisition only covered a 60° gantry rotation that did not include any vertical images (FIG. 11a). Acquisition of the first vertical image 15 sec into the treatment improved the accuracy to the same level as for 20 sec and 30 sec pre-treatment imaging.

FIG. 14b shows the distributions of 3D RMS errors in the trajectory estimations with pre-treatment imaging of 10 sec, 20 sec and 30 sec, and Table 4 presents the corresponding mean and maximum RMS errors and the percentages of trajectories with 3D RMS errors larger than 1 mm.

TABLE 4

| Pre-treat imaging | Mean RMS error (mm) | | | | Maximum RMS error (mm) | | | | >1 mm |
| --- | --- | --- | --- | --- | --- | --- | --- | --- | --- |
|  | LR | CC | AP | 3D | LR | CC | AP | 3D |  |
| 10 s | 0.15 | 0.0003 | 0.29 | 0.25 | 3.0 | 0.05 | 3.8 | 4.8 | 1.4 |
| 20 s | 0.13 | 0.0003 | 0.18 | 0.22 | 2.6 | 0.03 | 3.7 | 4.5 | 0.8 |
| 30 s | 0.13 | 0.0003 | 0.19 | 0.23 | 2.0 | 0.03 | 3.2 | 3.8 | 0.9 |

Figure 15:
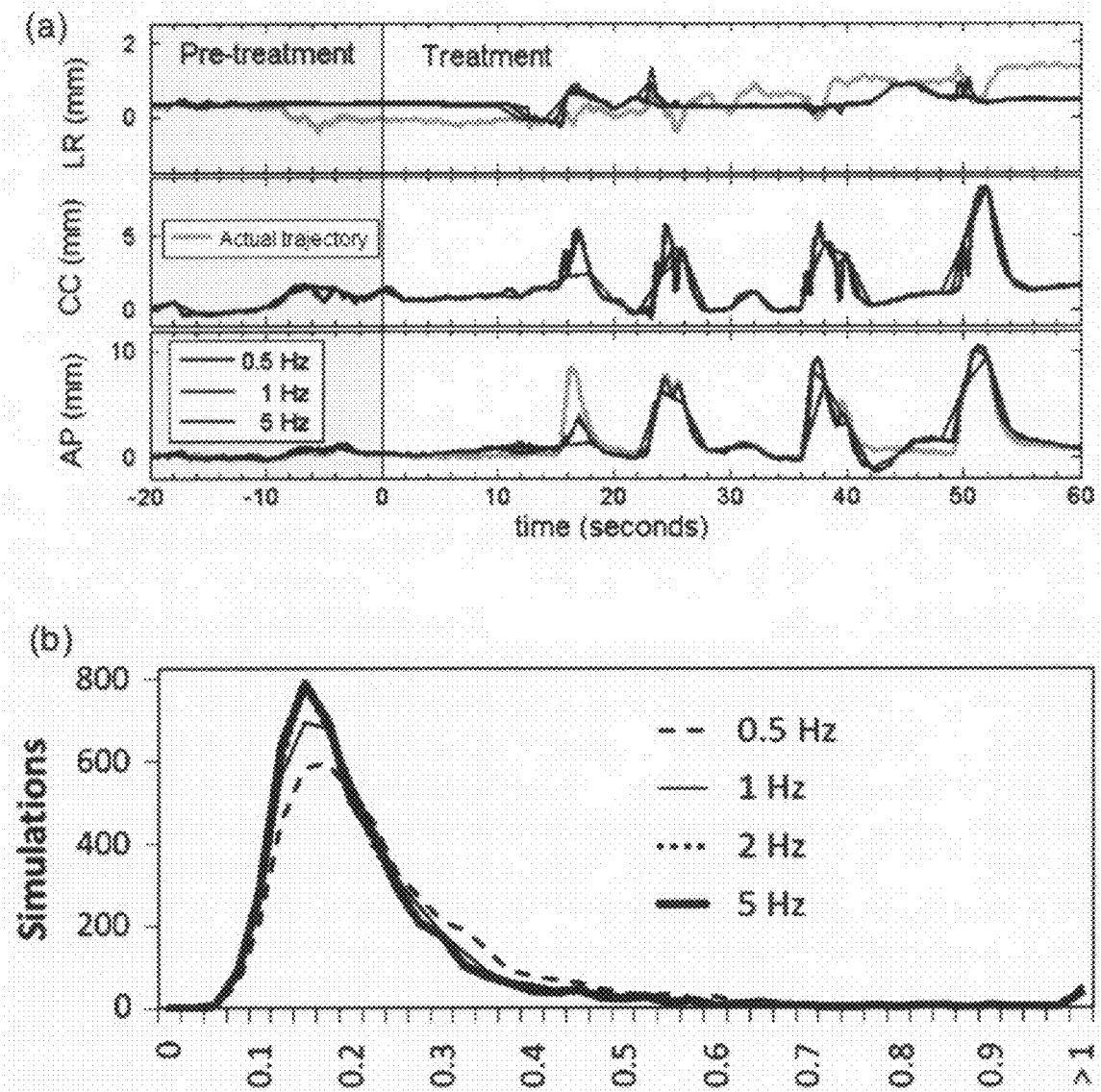
FIGS. 15a-15b show a comparison of real-time trajectory estimation with imaging at 0.5, 1, 2, and 5 Hz, and the corresponding distributions of 3D RMS errors, according to the present invention.

FIG. 15a shows a trajectory with frequent prostate displacements and estimations of the trajectory for a 1 min treatment with imaging at 0.5, 1 and 5 Hz. The pre-treatment duration is 20 sec and the PDF is dynamically updated. While the lower frequency imaging naturally failed to resolve fine structures beyond the temporal image resolution, the overall features are the same for all three estimations. This is also reflected by the relatively modest deterioration of the RMS error distribution with reduced imaging frequency (see distributions in FIG. 15b and Table 5).

Table 5 shows impact of the imaging frequency. Mean and maximum of RMS error and percentage of trajectories with vector RMS errors exceeding 1 mm.

TABLE 8

| Imaging frequency | Mean RMS error (mm) | | | | Maximum RMS error (mm) | | | | >1 mm |
| --- | --- | --- | --- | --- | --- | --- | --- | --- | --- |
|  | LR | CC | AP | 3D | LR | CC | AP | 3D |  |
| 0.5 Hz | 0.16 | 0.0006 | 0.20 | 0.26 | 3.4 | 0.13 | 3.6 | 4.5 | 1.1 |
| 1 Hz | 0.13 | 0.0003 | 0.18 | 0.23 | 2.6 | 0.03 | 3.7 | 4.5 | 0.8 |
| 2 Hz | 0.13 | 0.0003 | 0.18 | 0.23 | 2.8 | 0.05 | 3.7 | 4.6 | 0.8 |
| 5 Hz | 0.13 | 0.0003 | 0.18 | 0.22 | 2.6 | 0.03 | 3.7 | 4.5 | 0.8 |

Figure 16:
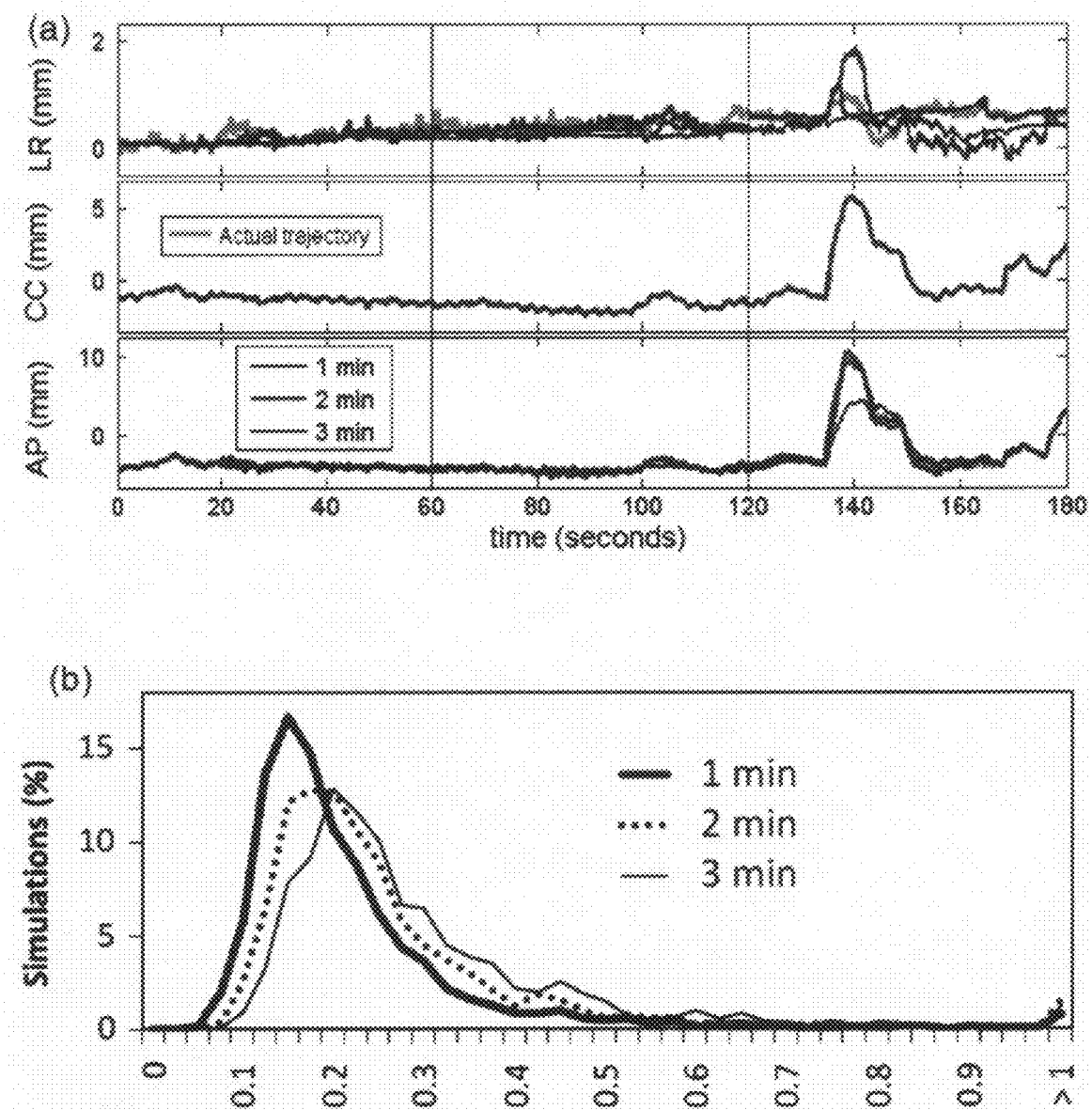
FIGS. 16a-16b shows a comparison of real-time trajectory estimation for treatments of 1, 2 and 3 min, and the corresponding distributions of 3D RMS errors, according to the present invention.
Figure 17:
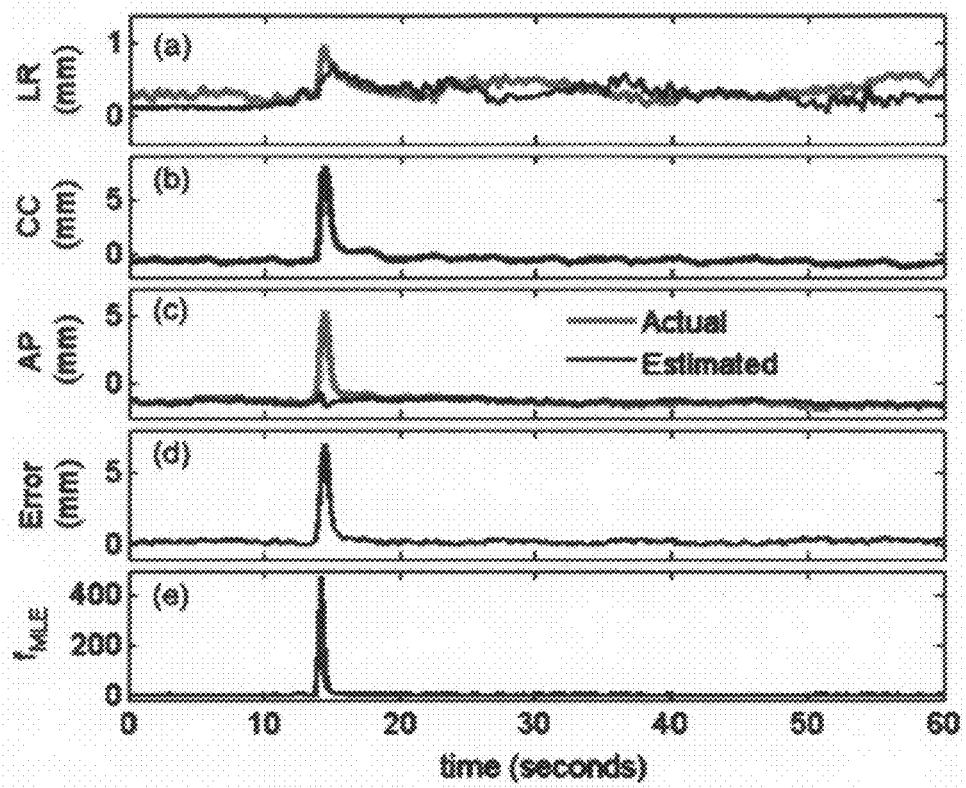
FIGS. 17a-17e show a trajectory with a large estimation error in the AP direction approximately 15 sec into the treatment, according to the present invention.

FIG. 16a gives an example of trajectory estimation with the dynamic PDF for treatments of 1, 2 and 3 min, and FIG. 16b shows the corresponding distributions of 3D RMS errors. The anterior prostate motion occurring after 140 sec is estimated slightly worse for the 2 min treatment and markedly worse for the 3 min treatment compared to the 1 min treatment. As seen in FIG. 16b and in the summarizing quantities in Table 6, prolonged treatment time generally resulted in less accurate trajectory estimations.

Table 6 shows the impact of the treatment duration. Mean and maximum of RMS error and percentage of trajectories with vector RMS errors exceeding 1 mm.

TABLE 6

| Treatment duration | Mean RMS error (mm) | | | | Maximum RMS error (mm) | | | | >1 mm |
|---|---|---|---|---|---|---|---|---|---|
| | LR | CC | AP | 3D | LR | CC | AP | 3D | |
| 1 min (n = 4728) | 0.13 | 0.0003 | 0.18 | 0.22 | 2.6 | 0.03 | 3.7 | 4.5 | 0.8 |
| 2 min (n = 2227) | 0.15 | 0.0004 | 0.23 | 0.27 | 2.4 | 0.04 | 3.5 | 4.2 | 1.5 |
| 3 min (n = 1390) | 0.17 | 0.0004 | 0.25 | 0.30 | 1.7 | 0.01 | 3.6 | 4.0 | 1.2 |

FIGS. 17a-17e show a trajectory with a large estimation error in the AP direction approximately 15 sec into the treatment. As seen in the lower part of the figure, the occurrence of this error coincides with an increase in the objective function term $f_{MLE}$. This is a frequent observation. This is further illustrated in FIGS. 18a-18b, in which each point shows either the RMS error, the 95th percentile error, the 99th percentile error or the maximum error for an $f_{MLE}$ bin as a function of the mean $f_{MLE}$ value for that bin. All four quantifications of the estimation accuracy increased with increasing $f_{MLE}$. This increase is almost monotonous for the RMS error, the 95th percentile error and the 99th percentile error (FIG. 18a), while less regular variations occurred for the maximum error (FIG. 18b).

Figure 18:
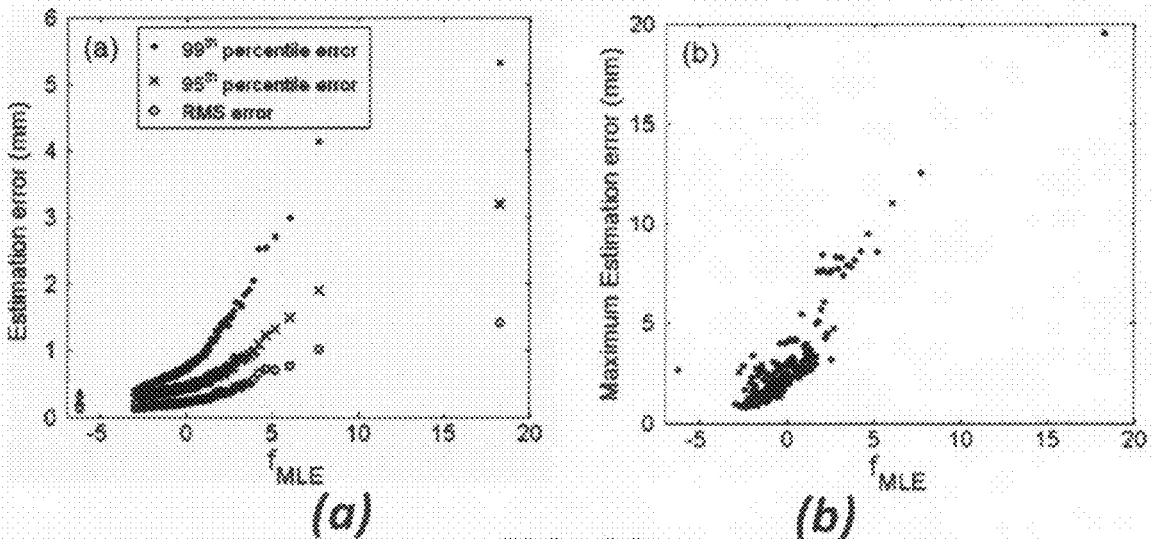
FIGS. 18a-18b show the RMS error, the 95th percentile error, the 99th percentile error or the maximum error for an $f_{MLE}$ bin as a function of the mean $f_{MLE}$ value for that bin, according to the present invention.

The relationship in FIG. 18 and the fact that $f_{MLE}$ is calculated for each image during the real-time trajectory estimation provide a tool for real-time assessment of the estimation accuracy. As an example, the 99th percentile estimation error is always below 2 mm when $f_{MLE}$ is smaller than 3.5 (FIG. 18a). This is the case for 96% of the images.

This aspect of the invention extends the previous trajectory estimation from retrospective analysis of CBCT projections to real-time prostate position estimation with a single imager during arc treatment. It opens the way for real-time target tracking with a single imager. Despite a clear loss in accuracy when only previously acquired images are available for PDF estimation (FIG. 12b), the method still provides good real-time trajectory estimations with RMS errors smaller than 1 mm in 99.2% of the 1 min treatments and more than 98.5% of the 2 or 3 min treatments. If the 2 and 3 min arc treatments are delivered in two or three arcs rather than one arc, the accuracy is similar to the 1 min single arc treatments.

The accuracy depended only modestly on the imaging frequency, which could be reduced to 1 Hz with only negligible loss in position estimation accuracy. It would result in a total of 80 images for a 1 min treatment with 20 sec pre-treatment imaging. This is a relatively small number of images considering that a CBCT scan often is based on more than 600 projection images Although the two static real-time PDFs are less accurate than the dynamically updated PDF, they still offer a marked improvement compared to no estimation of the unresolved motion (compare Tables 2 and 3). Certain generic motion patterns for prostate such as small LR motion and strong correlation between CC and AP motion make the use of a population-based PDF possible. The population-based PDF is slightly inferior to the individualized PDF determined from pre-treatment images for the majority of the simulations, but it is more robust with smaller maximum errors and fewer outliers with 3D RMS errors above 1 mm.

The exemplary simulations in the present invention are based purely on a single rotating imager, which could be a kV imager mounted perpendicular to the treatment beam. In this arrangement, continuous MV portal images could be acquired throughout the arc treatment without additional patient dose. Even the most modulated arc treatment would allow visibility of implanted prostate markers in a portion of these portal images since no part of the prostate would be blocked by MLC leaves during the entire treatment. The projected marker position in these portal images could easily be included in the prostate trajectory estimation, which should improve the accuracy. The portal images could either enter the MLE objective function in the same way as the kV images for improved PDF estimation or, if synchronized with orthogonal kV images, be used for exact 3D target position determination by triangulation.

As shown in FIG. 18, high values of the objective function term $f_{MLE}$ correlated with larger estimation errors. A high value of $f_{MLE}$ for an image means that the observed prostate projection in the image has a very low probability according to the estimated 3D PDF. This could either be true (i.e. the prostate has really moved to a position with very low probability) or it could be indicating that the estimated PDF does not give a good description of the prostate position distribution. The latter is a likely explanation for the observed correspondence between large values of ƒMLE and large estimation errors. This correspondence provides a tool for real-time assessment of the estimation accuracy for each individual position estimation along a trajectory. This could be used to perform interventions in the treatment (e.g. pause of the beam) if $f_{MLE}$ exceeds a preset threshold value for a preset time duration during the treatment. Reestablishment of the PDF might be needed prior to resumption of the treatment.

Figure 19:
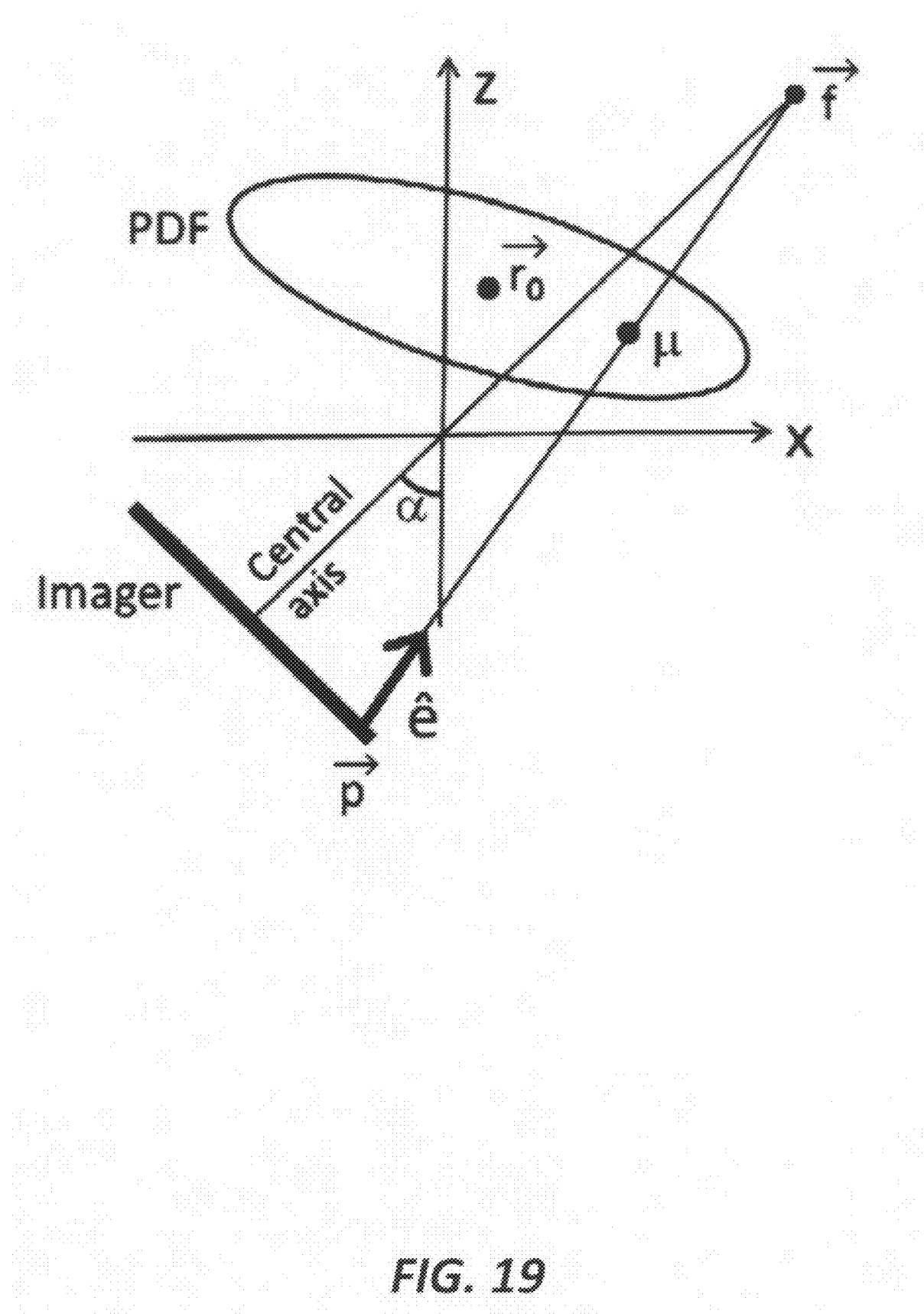
FIG. 19. shows an imager system and Gaussian target PDF in the patient coordinate system, according to the present invention.

FIG. 19. Shows an imager system and Gaussian target PDF in the patient coordinate system. Positive x and z correspond to left and anterior directions for a head-first supine patient. The origin of the coordinate system coincides with the isocenter and the y-axis points into the page (cranial direction). α is the rotation angle of the imager. The spatial points $\vec{r}_0$, and $\vec{f}$ and $\vec{p}$ are the mean position of the PDF, the focus point of the imager system and the target projection point on the imager, respectively. ê is a unit vector along the ray line from $\vec{p}$ to $\vec{f}$ and μ is the expectation value of the 1D Gaussian along this ray line.

The mathematical framework for estimation of the 3D target position from a 2D projection and a 3D Gaussian PDF, according to the current invention is provided in an exemplary simplified case with mean target position $$\vec{r}_0 = \begin{pmatrix} x_0 \\ y_0 \\ z_0 \end{pmatrix} = \begin{pmatrix} 0 \\ 0 \\ 0 \end{pmatrix}$$

In the following, the theory is extended to a finite mean target position and inclusion of the objective function $F_{MLE}$ for MLE estimation of the PDF. The following derivation will be made in the patient coordinate system. It results in formulae that are more efficient for MLE optimization because it avoids repeated rotation of the 3D PDF to imager coordinates for each step in the MLE optimization. Furthermore, the resulting formulae are more easily extended beyond the geometry of coplanar imaging with a gantry-mounted imager, for example to room-mounted imagers. The room coordinate system and the imager geometry are defined in FIG. 19. The covariance matrix $\bar{\bar{A}}$ of the target positions is defined as follows:

$$\bar{\bar{A}} = \begin{pmatrix} \text{var}(LR) & \text{cov}(LR, CC) & \text{cov}(LR, AP) \\ \text{cov}(CC, LR) & \text{var}(CC) & \text{cov}(CC, AP) \\ \text{cov}(AP, LR) & \text{cov}(AP, CC) & \text{var}(AP) \end{pmatrix}, \quad (A.1)$$

where var denotes the variance of the target position in the principal directions and cov denotes the covariance of the target motion along each axes pair. The 3D Gaussian PDF of target positions can be expressed as follows in terms of the inverse covariance matrix $$\bar{\bar{B}} = \bar{\bar{A}}^{-1} \quad (A.2)$$

$$g(x, y, z) = \frac{\sqrt{\det \bar{\bar{B}}}}{\sqrt{(2\pi)^3}} \exp\left[-1/2(\vec{r} - \vec{r}_0)^T \bar{\bar{B}}(\vec{r} - \vec{r}_0)\right]$$

Here, $\vec{r} = \begin{pmatrix} x \\ y \\ z \end{pmatrix}$ is the 3D target position and $\vec{r}^T = (x\ y\ z)$ is its transpose.

The 3D Gaussian in equation (A.2) is defined by nine parameters, namely the three components of $\vec{r}_0$ and the six different elements of $\bar{\bar{B}}$. These are the parameters that are estimated in the MLE optimization.

The derivation follows three steps: (1) determination of a parametric equation for the ray line in FIG. 19, (2) substitution of this parametric equation into the 3D Gaussian PDF and (3) rearrangement of the resulting equation to obtain the functional form of a 1D Gaussian (i.e. equation (A.3)) and identifying the expressions for the scaling factor K, the standard deviation $\sigma$ and the mean position $\mu$:

$$g_{1D}(t) = K \times \exp\left(-\frac{(t-\mu)^2}{2\sigma^2}\right) \quad (A.3)$$

In patient coordinates, the projection point $\vec{p}$ on the imager (FIG. 19) is given as follows:

$$\vec{p} = \begin{pmatrix} x_p \cos\alpha - (SDD - SAD)\sin\alpha \\ y_p \\ -x_p \sin\alpha - (SDD - SAD)\cos\alpha \end{pmatrix} \quad (A.4)$$

Here, SAD and SDD denote the source-axis distance and the source-detector distance, respectively, and $(x_p, y_p)$ is the projected target position in imager coordinates. The focus point of the imager system is given by $$\vec{f} = \begin{pmatrix} SAD\sin\alpha \\ 0 \\ SAD\cos\alpha \end{pmatrix} \quad (A.5)$$

The unit vector $\hat{e}$ in FIG. 19 along the ray line from $\vec{p}$ to $\vec{f}$ is then given by $$\hat{e} = \frac{\vec{f} - \vec{p}}{|\vec{f} - \vec{p}|} \quad (A.6)$$

and the ray line can be parameterized as follows:

$$\vec{L} = \vec{p} + \hat{e}t,\ t \in \mathfrak{R}. \quad (A.7)$$

By inserting the parametric equation (A.7) into equation (A.2) and performing some rearrangements to obtain the functional form of equation (A.3), the following expressions for $\sigma$, $\mu$ and K are obtained:

$$\sigma = 1 / \sqrt{\hat{e}^T \bar{\bar{B}} \hat{e}} \quad (A.8)$$

$$\mu = \left((\vec{r}_0 - \vec{p})^T \bar{\bar{B}} \hat{e}\right) / \left(\hat{e}^T \bar{\bar{B}} \hat{e}\right) \quad (A.9)$$

$$K = \frac{\sqrt{\det \bar{\bar{B}}}}{\sqrt{(2\pi)^3}} \exp\left[-1/2(\vec{p} + \hat{e}\mu - \vec{r}_0)^T \bar{\bar{B}}(\vec{p} + \hat{e}\mu - \vec{r}_0)\right] \quad (A.10)$$

Note that K is just the value of g(x, y, z) (equation (A.2)) at the expectation value $\mu$ along the ray line in FIG. 19 (expression (A.7) with t=$\mu$).

For a different imager geometry, e.g. for room-mounted imagers, the expressions for $\vec{p}$ and $\vec{f}$ would differ from equations (A.4) and (A.5), but equations (A.6)-(A.10) would still be valid.

The probability $P(x_p, y_p)$ for the target to be projected into a small area $dx_p\,dy_p$ around the point $(x_p, y_p)$ is given by the line integral of the PDF along the ray line as follows:

$$P(x_p, y_p) = \left[\int_{-\infty}^{\infty} K \times \exp\left(-\frac{(t-\mu)^2}{2\sigma^2}\right) dt\right] dx_p\,dy_p = \quad (A.11)$$

$$K\sqrt{2\pi}\ \sigma dx_p dy_p$$

Maximum likelihood estimation of g(x, y, z)

In the first step of the target trajectory estimation from a series of projections $(x_{pi}, y_{pi})$, the 3D Gaussian PDF is estimated by MLE. Here, the nine unknown parameters of the PDF are selected such that the total probability, i.e. the product $\Pi_i P(x_{pi}, y^{pi})$ of all considered projections $(x_{pi}, y_{pi})$, is maximized. Since this is equivalent to minimizing $-\log [\Pi_i P(x_{pi}, y_{pi})]$, the objective function to be minimized in the MLE optimization is given by $$F_{MLE} = \quad \text{(A.12)}$$
$$-\sum_i \log[K_i \sqrt{2\pi}\, \sigma_i dx_p dy_p] = -\sum_i \log[K_i^* \sqrt{2\pi}\, \sigma_i] = \sum_i f_{MLE,i}$$

where the sum includes all images i considered in the MLE optimization. In equation (A.12), we have assumed that both $x_p$ and $dy_p$ are of unit length and we have defined $K^*_i$ as $K_i$ multiplied by the unit length squared. In the last expression, we have introduced the notation $f_{MLE,i} = -\log[K^*_i \sqrt{2\pi}\sigma_i]$ for the contribution of image i to the objective function. The MLE optimization is made under the condition that matrix $\overline{B}$ is positive definite, which ensures that it is invertible. The inverse of the optimized $\overline{B}$, i.e. the optimized covariance matrix, directly gives the MLE-estimated values for the variances and covariances via equation (A.1) or, equivalently, the standard deviation of the target position and the correlation coefficient for target motion along each direction pair.

Estimation of the 3D Target Position

When the PDF has been estimated by MLE, it can be used to estimate the 3D target position for an image. Here, the parameter t in equation (A.3) is estimated as its expectation value μ, which is given in equation (A.9). Insertion of t=μ in equation (A.7) directly gives the estimated 3D target position in the patient coordinate system.

The present invention provides a method for estimation of retrospective and real-time 3D target position by a single imager. The invention includes imaging a target on at least one 2D plane to determine 2D position and/or position components of the target, and resolving a position and/or position component along at least one imager axis of the target using a spatial probability density.

According to one aspect of the invention, the spatial probability density for the target position comprises a Gaussian probability distribution.

In a further aspect, the spatial probability density is centered at an isocenter of a treatment unit, at a center of a patient coordinate system, or any other point in space.

In another aspect of the invention, the spatial probability density is determined from a variance and covariance matrix of the target position.

According to another aspect of the invention, determining the 2D position includes projecting the target into a point on at least a 2-D imager plane disposed on at least one imaging angle relative to a vertical direction, where the target lies along a ray line between the point on the imager plane and a beam source of an imager.

In yet another aspect of the invention, resolving the position component along an imager axis includes using a maximum likelihood estimation to determine a best fit of projection data to a spatial Gaussian distribution of a probability density of the target position, and determining an expectation value or the target position along the ray line. Here, an uncertainty in target position estimation along the ray line is determined from a one-dimensional probability density for the target along the ray line. Further, more than one imager can be used without being synchronized. Additionally, the Gaussian distribution includes a mean target position, a standard deviation of the mean target position, and correlation coefficients of paired degrees of freedom of the target position. Here, the mean target position, the standard deviation, and the correlation coefficients are used for position inclusive radiotherapy. In another aspect, the expectation value is used to estimate an unresolved target position component as a function of a resolved the target position component. Further, the expectation value is used to determine a trajectory of the target, where the determined target trajectory is a real-time determination and the determined target trajectory is used for gating and target tracking during radiotherapy. Here, the gating and target tracking is done in real-time using a dynamic multi-leaf collimator, a treatment couch or other device to align the treatment beam and the target.

In another aspect of the invention, the imaging of target on the 2D plane is done in a time ranging from continuous imaging to 1 minute intervals.

In yet another aspect of the invention, the imager can include at least one x-ray imager, where the at least one x-ray imager is operated independently or simultaneously and can be a kilovolt x-ray imager, a megavolt x-ray imager.

In a further aspect, a beam of the imager is disposed perpendicular to a treatment beam.

According to another aspect of the invention, the estimation is done in real-time during a treatment therapy such as intensity modulated arc therapy, arc radiotherapy, intensity modulated radiotherapy from fixed fields or conformal radiotherapy.

The present invention has now been described in accordance with several exemplary embodiments, which are intended to be illustrative in all aspects, rather than restrictive. Thus, the present invention is capable of many variations in detailed implementation, which may be derived from the description contained herein by a person of ordinary skill in the art. For example, since the probability-based method relaxes the requirement of simultaneous image acquisition at different angles for 3D target position determination, it allows dual imager systems to estimate the 3D position also in periods when only one imager can be used. Some relevant examples are (1) kV/MV imagers when the target is blocked in MV images due to intensity modulation, (2) kV/kV imagers when one imager is blocked by the treatment unit, or (3) kV/kV imagers without the capability of simultaneous acquisition because the imagers share the same x-ray generator. Internal landmarks used for the probability based method could include implanted markers or internal radioopaque objects and tissues. Using two of more of the landmarks together would allow the estimation of rotation and/or deformation of all or part of the patient's anatomy.

All such variations are considered to be within the scope and spirit of the present invention as defined by the following claims and their legal equivalents.

What is claimed is:

1. A method for estimation of retrospective and real-time 3D target position by a single imager comprising:
   a. using a single imager to image a 2D plane of a target, wherein a 2D planar image of said target is used to resolve 2D target position components of said target; and
   b. using a probability density function (PDF) estimated by maximum likelihood estimate (MLE), or using a population based PDF for estimating 3D target position;
      wherein using said PDF estimated by MLE comprises:
      i. using an assumed 3D PDF for a 3D position of said target to determine a probability $P(u, v, \alpha)$ for said target to be projected into a point $(u, v)$ on said imager positioned at angle $\alpha$;
      ii. using a probability $P(u, v, \alpha)$ of said 2D target position components in said MLE to estimate said PDF as a PDF that best fits said 2D components, wherein said PDF comprises at least one of a left-right mean position($\mu_{LR}$), a cranio-caudal mean position($\mu_{CC}$), an anterior-posterior mean position ($\mu_{AP}$), a left-right standard deviation ($\sigma_{LR}$), a cranio-caudal standard deviation ($\sigma_{CC}$) an anterior-posterior standard deviation ($\sigma_{AP}$), a left-right —cranio-caudal correlation coefficient of motion ($\rho_{LR-CC}$), a left-right —anterior-posterior correlation coefficient of motion ($\rho_{LR-AP}$), or a cranio-caudal —anterior-posterior correlation coefficient of motion ($\rho_{CC-AP}$); and iii. using said PDF estimated by said MLE to estimate one said target position component disposed along an imager axis of said target, wherein an estimate of said 3D target position is made from said 2D target position components in said 2D planar image;

wherein using said population based PDF comprises:

i. using a population of 3D target position observations of a population of other targets to determine a 3D population-based PDF for said 3D position of said target; and ii. using said 3D population-based PDF to estimate one said target position component disposed along an imager axis of said target, wherein an estimate of said 3D target position is made from said 2D target position components in said 2D planar image.

2. The method for estimation of 3D target position of claim 1, wherein said PDF for said target position comprises a Gaussian probability distribution.

3. The method for estimation of 3D target position of claim 1, wherein said PDF is centered at a center of a patient coordinate system, or any other point in space.

4. The method for estimation of 3D target position of claim 1, wherein said PDF is determined from a variance and covariance matrix of said target position.

5. The method for estimation of 3D target position of claim 1, wherein resolving said position component along said imager axis of said target comprises using said maximum likelihood estimation to determine a best fit of projection data to a spatial Gaussian distribution of said PDF of said target position, and determining an expectation value or said target position along a ray line.

6. The method for estimation of 3D target position of claim 5, wherein an uncertainty in target position estimation along said ray line is determined from a one-dimensional probability density for said target along said ray line.

7. The method for estimation of 3D target position of claim 5, wherein more than one imager is used without being synchronized.

8. The method for estimation of 3D target position of claim 5, wherein said expectation value is used to estimate an unresolved said target position component as a function of a resolved target position component.

9. The method for estimation of 3D target position of claim 5, wherein said expectation value is used to determine a trajectory of said target.

10. The method for estimation of 3D target position of claim 9, wherein said determined target trajectory is a real-time determination.

11. The method for estimation of 3D target position of claim 9, wherein said determined target trajectory is used for gating and target tracking during radiotherapy.

12. The method for estimation of 3D target position of claim 11, wherein said gating and target tracking is done in real-time using a device to align a treatment beam and said target.

13. The method for estimation of 3D target position of claim 1, wherein a mean target position of said target, a standard deviation of said target position, and correlation coefficients of said target position are used for motion inclusive radiotherapy.

14. The method for estimation of 3D target position of claim 1, wherein said imaging of said target on said 2D plane is done in a time ranging from continuous imaging to 1 minute intervals.

15. The method for estimation of 3D target position of claim 1, wherein said imager is selected from the group consisting of an x-ray imager, wherein said x-ray imager is operated independently or simultaneously and is selected from the group consisting of a kilovolt x-ray imager and a megavolt x-ray imager.

16. The method for estimation of 3D target position of claim 1, wherein an estimation is done in real-time during a treatment therapy selected from the group consisting of intensity modulated arc therapy, arc radiotherapy, intensity modulated radiotherapy from fixed fields and conformal radiotherapy.

* * * * *